(12) United States Patent
DeFlores et al.

(10) Patent No.: US 8,526,002 B2
(45) Date of Patent: Sep. 3, 2013

(54) TWO-DIMENSIONAL FOURIER TRANSFORM SPECTROMETER

(75) Inventors: Lauren DeFlores, Cambridge, MA (US); Andrei Tokmakoff, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 530 days.

(21) Appl. No.: 12/676,536

(22) PCT Filed: Sep. 8, 2008

(86) PCT No.: PCT/US2008/010460
§ 371 (c)(1),
(2), (4) Date: Mar. 4, 2010

(87) PCT Pub. No.: WO2009/075702
PCT Pub. Date: Jun. 18, 2009

(65) Prior Publication Data
US 2010/0171952 A1    Jul. 8, 2010

Related U.S. Application Data

(60) Provisional application No. 60/967,889, filed on Sep. 8, 2008.

(51) Int. Cl.
*G01B 9/02* (2006.01)
*G01J 3/30* (2006.01)

(52) U.S. Cl.
USPC ............................ 356/451; 356/317

(58) Field of Classification Search
USPC ................. 356/452–456, 300–334
See application file for complete search history.

(56) References Cited

U.S. PATENT DOCUMENTS

| 2003/0016358 A1 | 1/2003 | Nagashima et al. |
| 2007/0018103 A1 | 1/2007 | DeCamp et al. |
| 2007/0152154 A1 | 7/2007 | DeCamp et al. |
| 2009/0161092 A1 | 6/2009 | Zanni et al. |

FOREIGN PATENT DOCUMENTS

| JP | 2000-275105 | 10/2000 |
| JP | 2003-194713 | 7/2003 |
| WO | WO 00/50859 | 8/2000 |

OTHER PUBLICATIONS

Selig et al., Inherently phase-stable coherent 2D spectroscopy using only conventional optics, Optical Society of America, pp. 1-3, Aug 14, 2008.
Khalil et al., Coherent 2D IR spectroscopy: Molecular Structure and Dynamics in Solution, J.Phys. Chem. A 2003, 107, 5258-5279, Jun. 19, 2003.
Xiong et al., Signal enhancement and background cancellation in collinear two-dimensional spectroscopies, Optics Letters, vol. 33, No. 12, Jun. 15, 2008.

*Primary Examiner* — Hwa Lee
(74) *Attorney, Agent, or Firm* — McCarter & English, LLP

(57) ABSTRACT

The present invention relates to a system and methods for acquiring two-dimensional Fourier transform (2D FT) spectra. Overlap of a collinear pulse pair and probe induce a molecular response which is collected by spectral dispersion of the signal modulated probe beam. Simultaneous collection of the molecular response, pulse timing and characteristics permit real time phasing and rapid acquisition of spectra. Full spectra are acquired as a function of pulse pair timings and numerically transformed to achieve the full frequency-frequency spectrum. This method demonstrates the ability to acquire information on molecular dynamics, couplings and structure in a simple apparatus. Multi-dimensional methods can be used for diagnostic and analytical measurements in the biological, biomedical, and chemical fields.

62 Claims, 37 Drawing Sheets

Two-dimensional Fourier Transform Infrared Spectroscopy in Pump-Probe Geometry
Rephasing + Non-rephasing
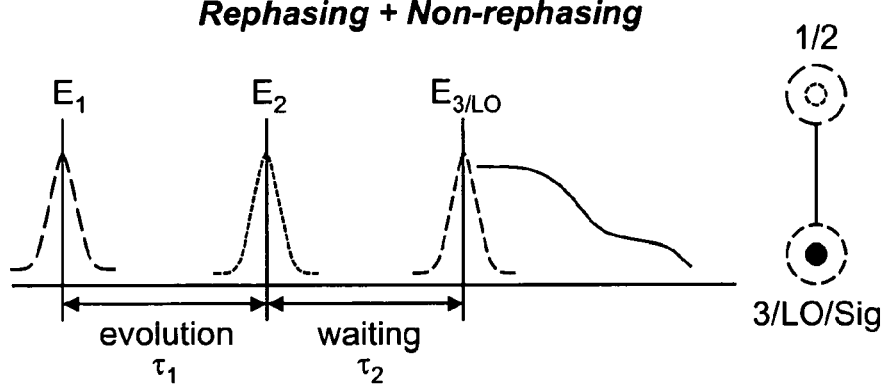
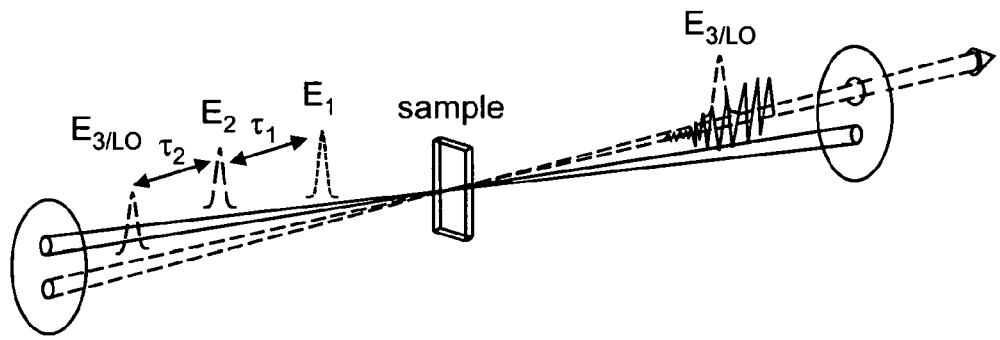
Unknowns (1)
$\tau_1 = 0$
Constraints (1)
Fit of 2D Projection to DPP
Additional Real-time Experimental Controls
Interferometric Autocorrelations
Stage Calibration
FIG. 2B

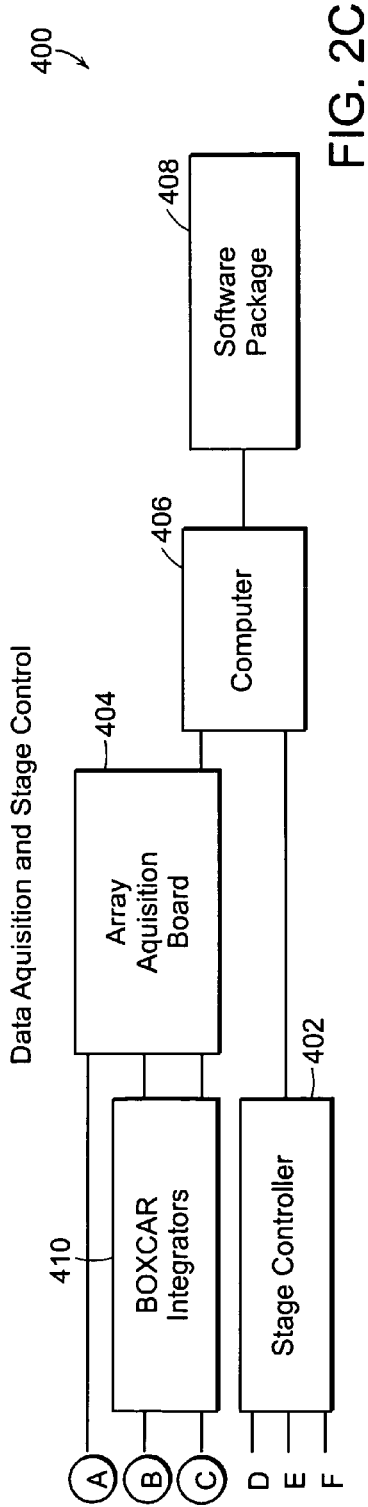

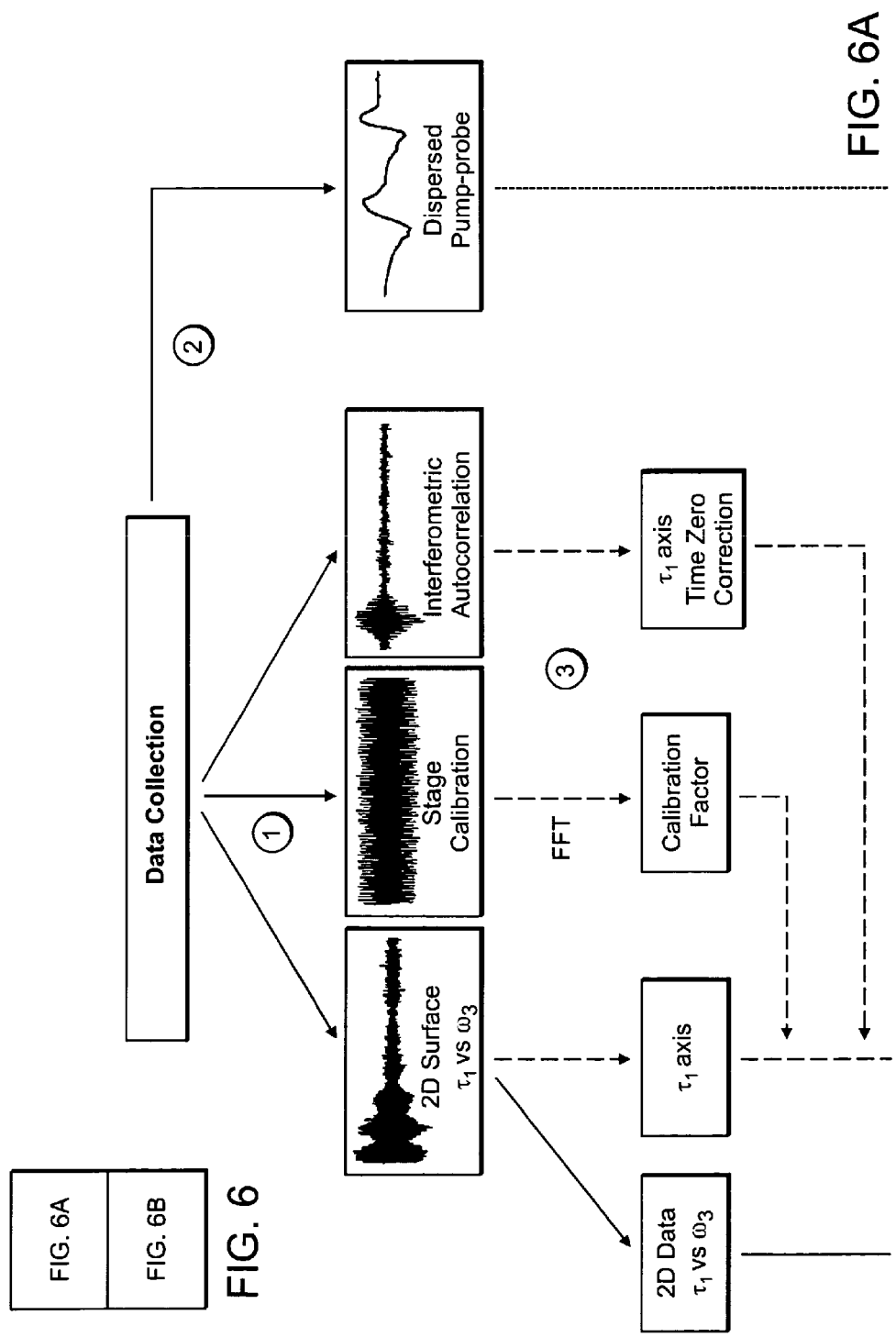

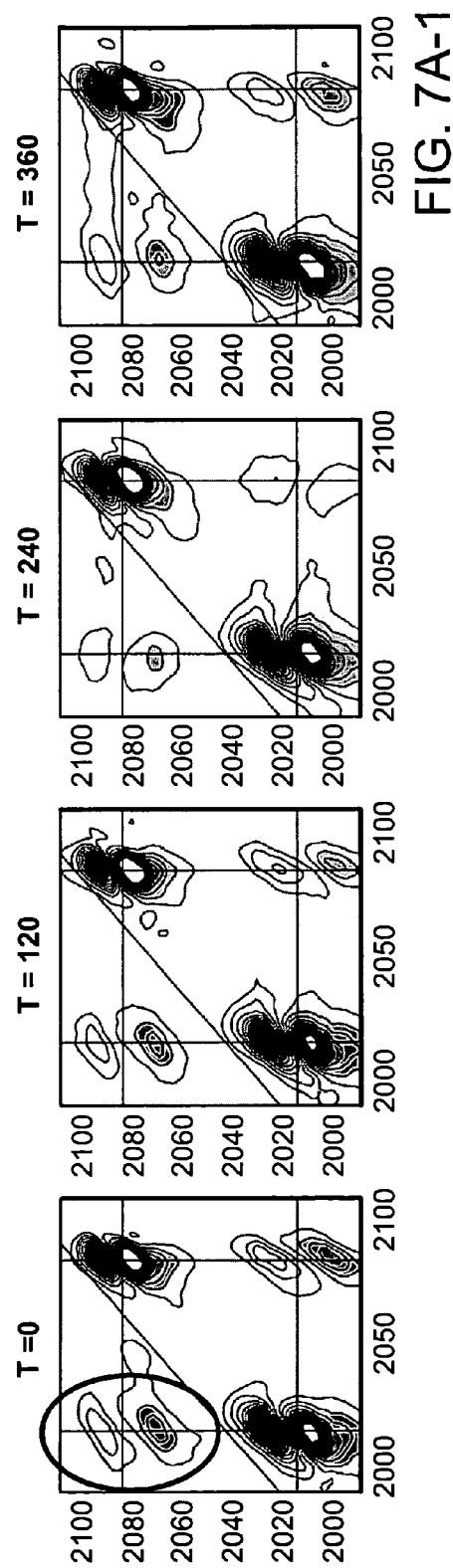

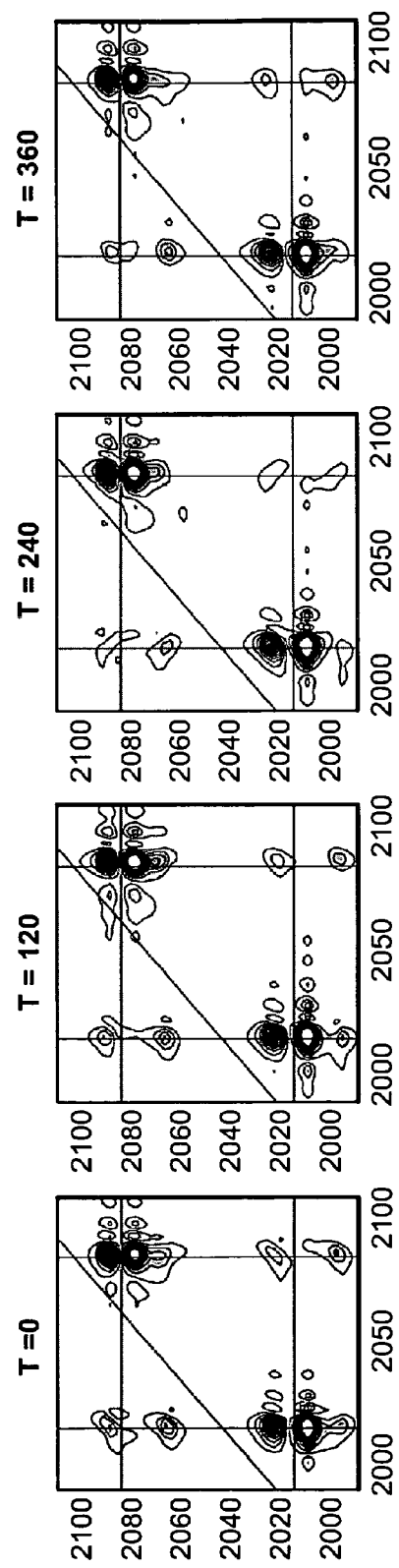

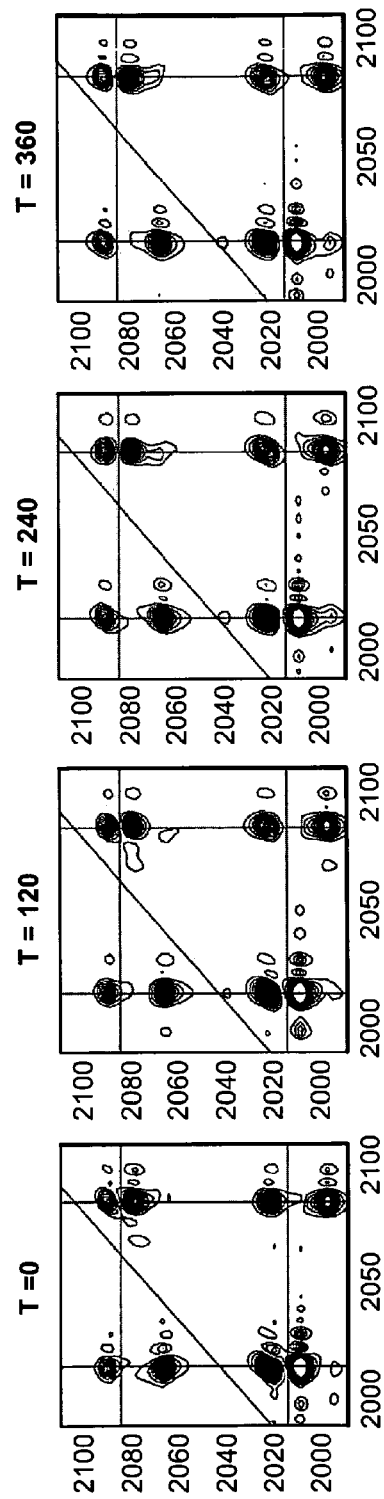

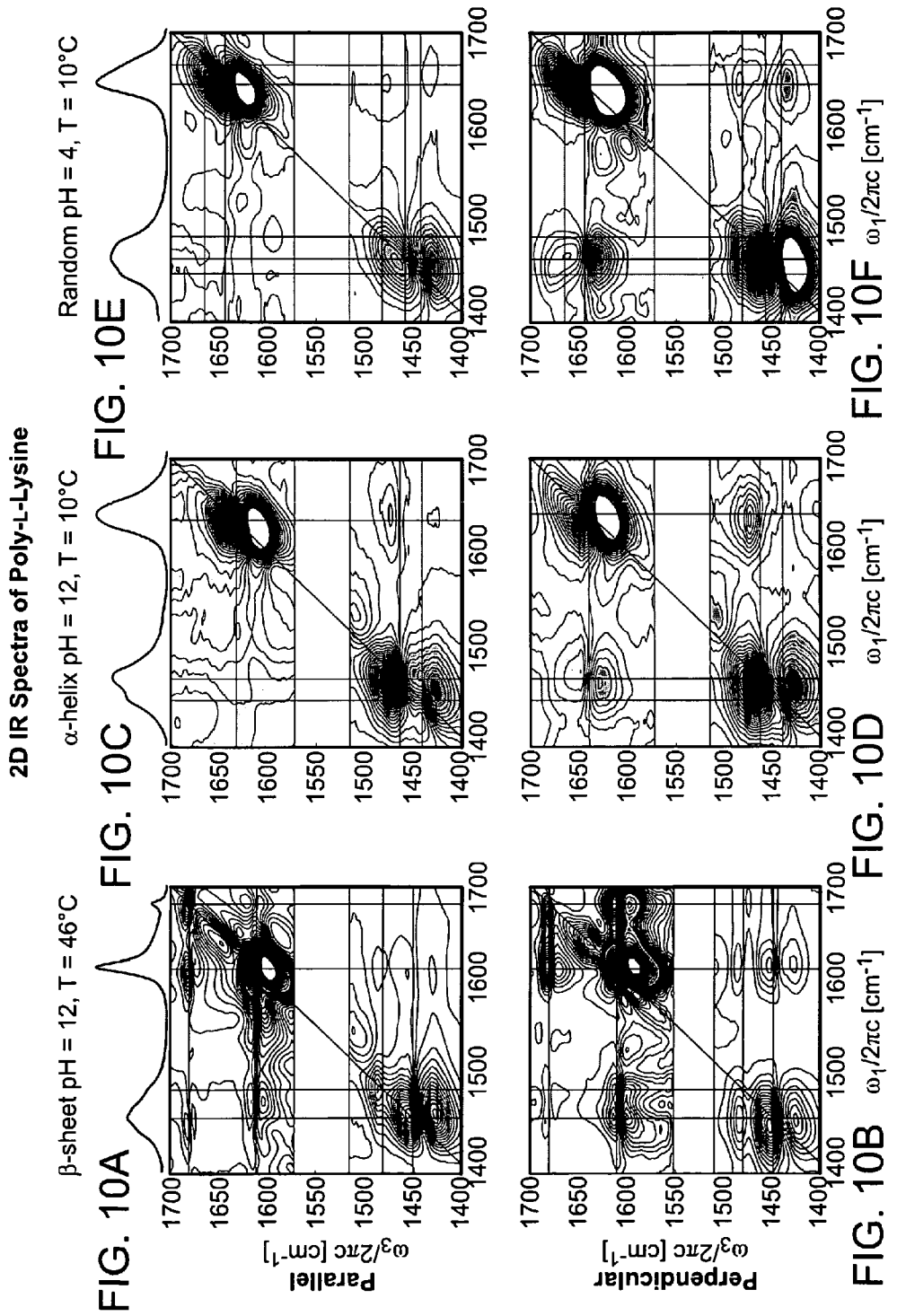

Calculated 2D IR Spectra of Idealized Secondary Structure
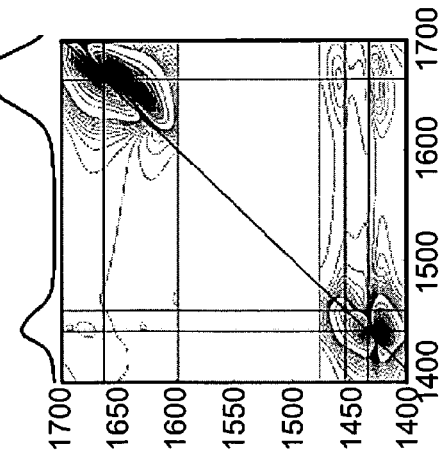
FIG. 12A  β-sheet
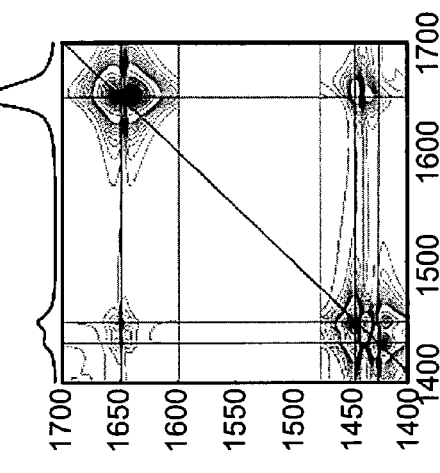
FIG. 12C  α-helix
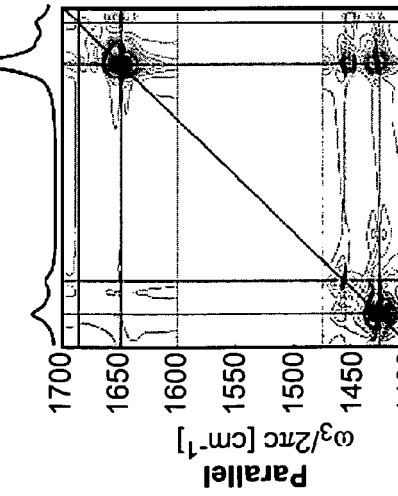
FIG. 12E  Random
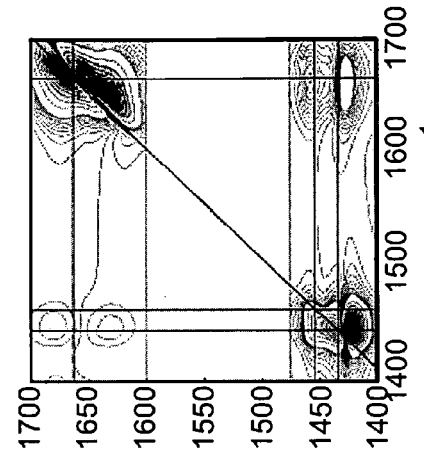
FIG. 12B
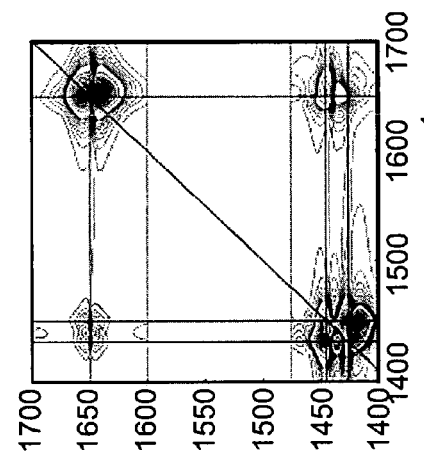
FIG. 12D
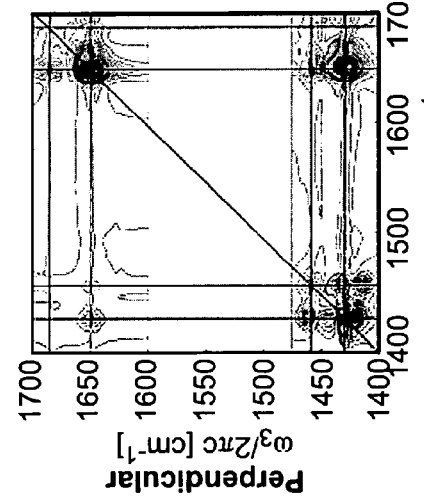
FIG. 12F

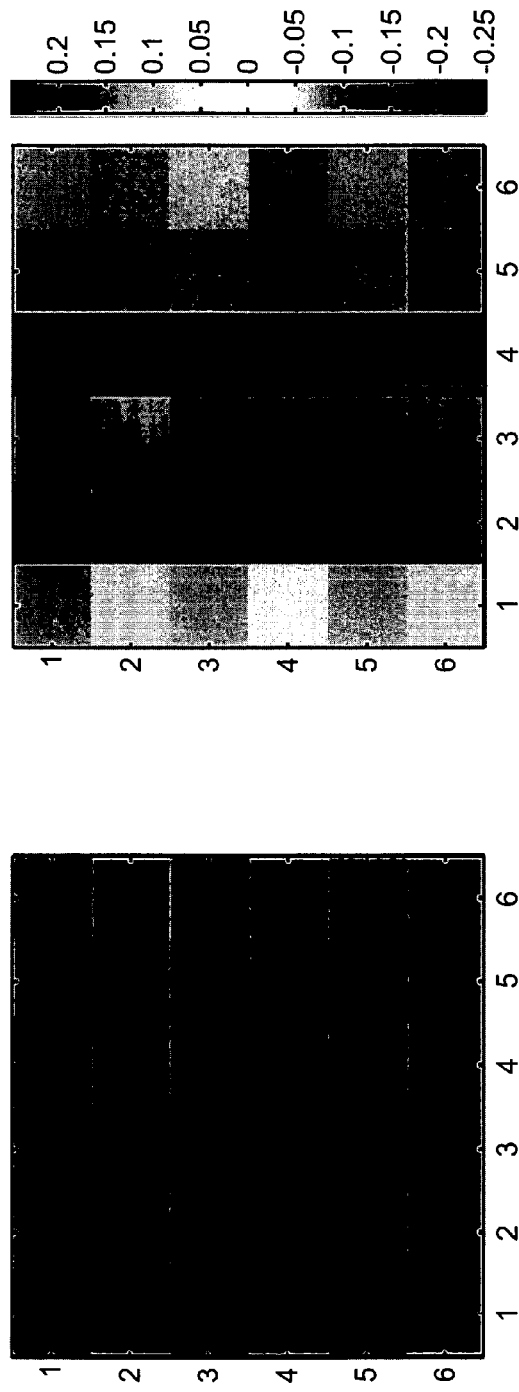
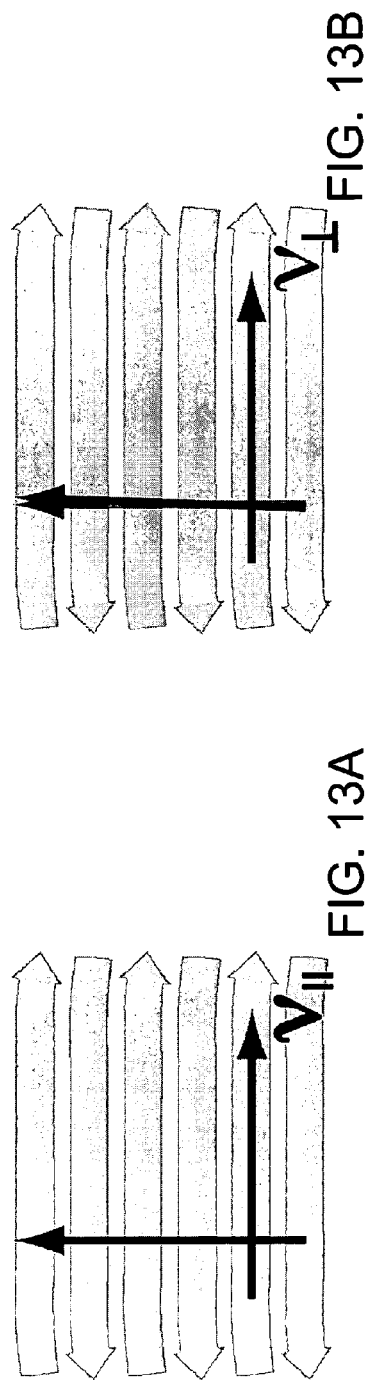
FIG. 13A
FIG. 13B

Amide II' α-helix Doorway Modes
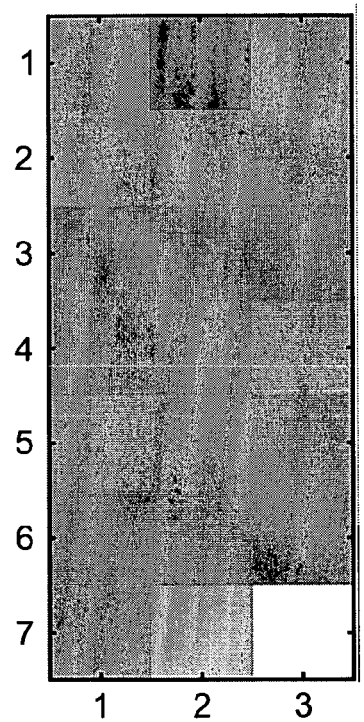
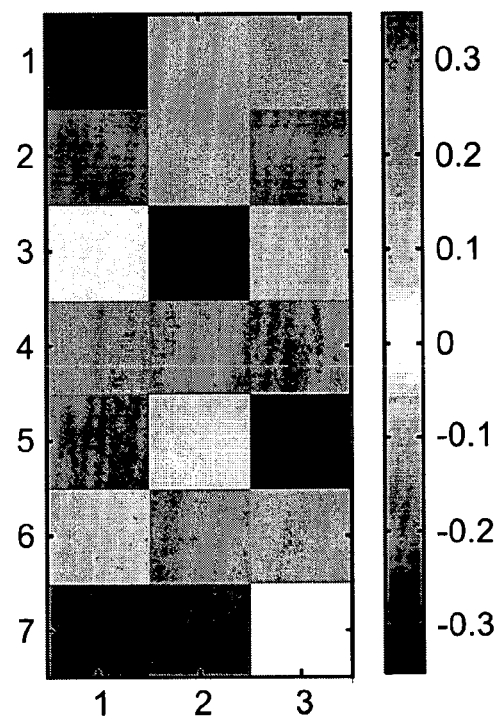
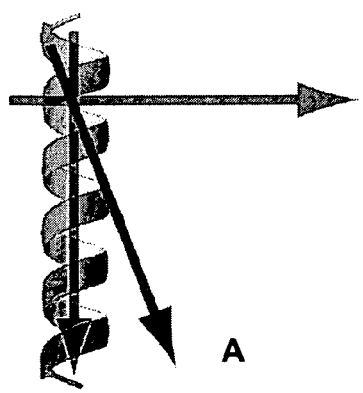
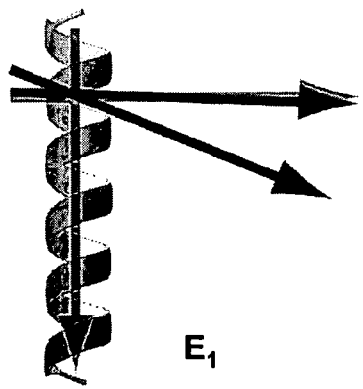
FIG. 13C          FIG. 13D

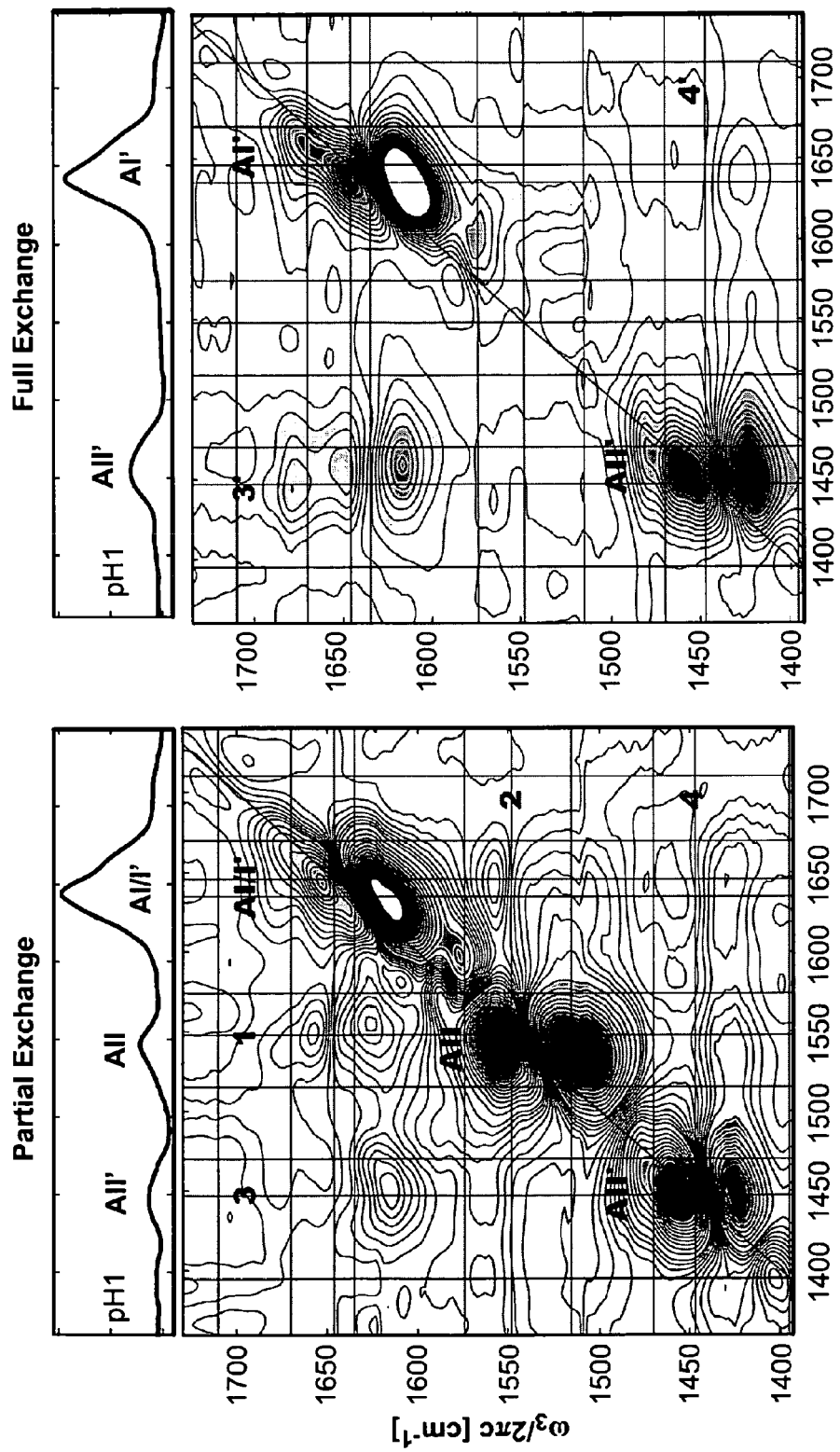

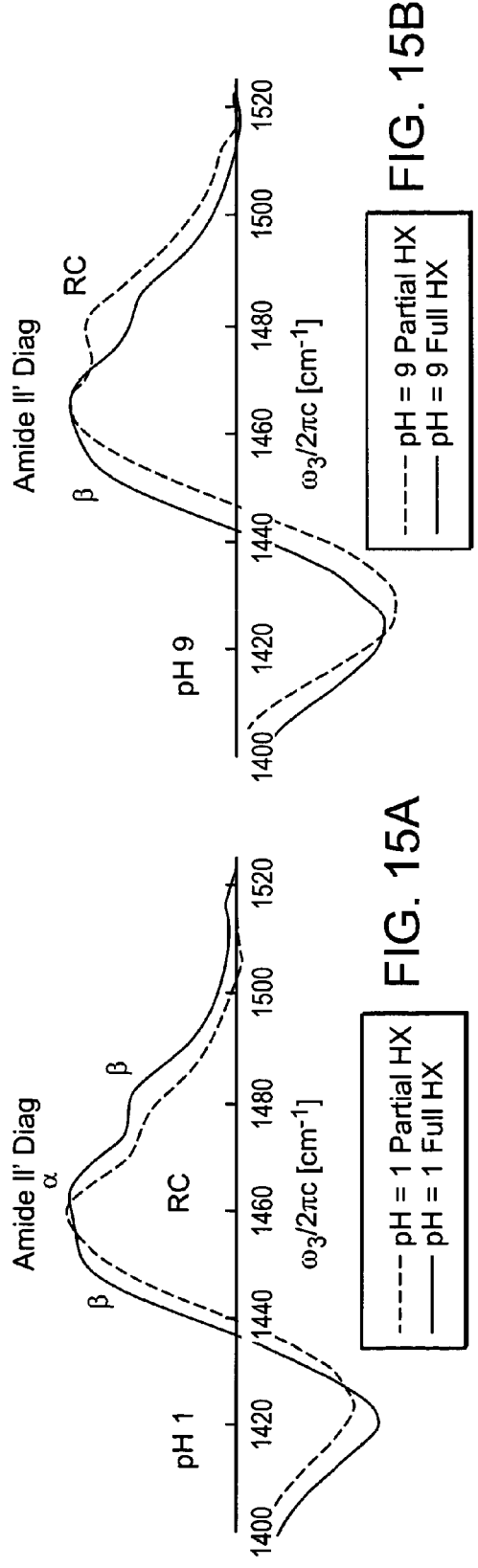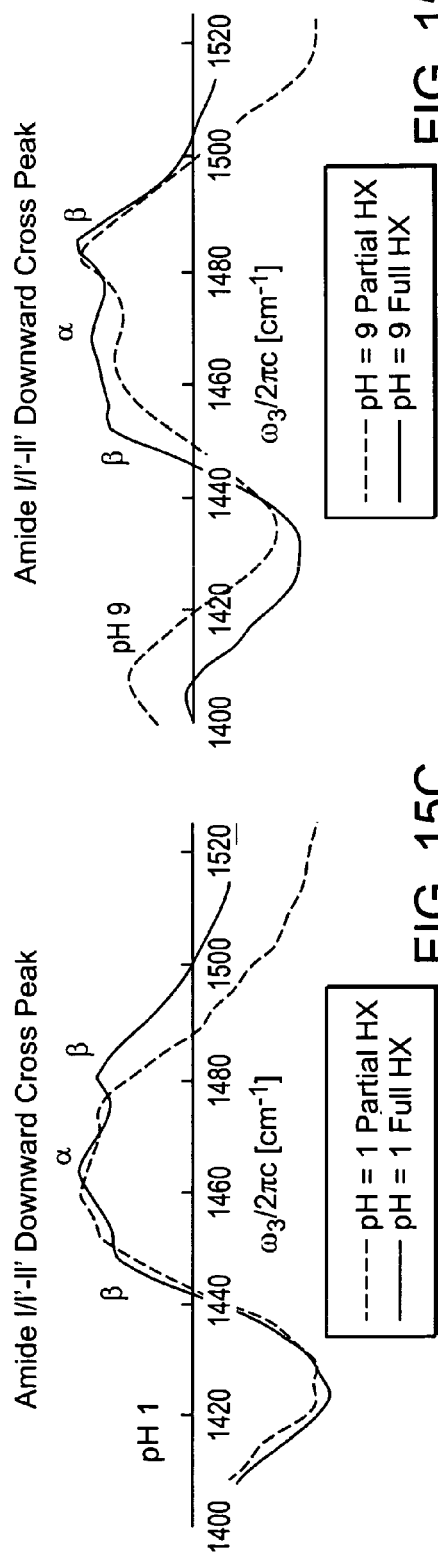

TWO-DIMENSIONAL FOURIER TRANSFORM SPECTROMETER

CROSS REFERENCE TO RELATED APPLICATIONS

This application claims the benefit of U.S. Provisional Application No. 60/967,889, filed Sep. 7, 2007, which is incorporated by reference herein.

STATEMENT REGARDING FEDERALLY SPONSORED RESEARCH

This invention was supported by grants from the National Science Foundation (CHE-0616575) and the U.S. Department of Energy (DE-FG02-99ER14988). The U.S. Government has certain rights in the invention.

BACKGROUND OF THE INVENTION

Multi-dimensional optical spectroscopy has developed as a method for characterizing materials in a variety of applications from biomedical applications to the semiconductor industry. To this point, though making a substantial mark with contributions to molecular and reaction dynamics, optical techniques have been limited due to the degree of complexity and expertise required for construction and use of the optical and infrared 2D FT spectrometers.

Typical 2D spectrometers require the use of four variably delayed pulses in which three beams are aligned in a "boxcar" geometry to achieve background-free phase matching of the 2D signal as shown in FIG. 1. The fourth is used for external heterodyne detection of the signal field for acquiring phase and amplitude information. Commonly, a fifth beam is introduced and aligned in the forth corner of the "boxcar" to help with alignment of the signal field and for acquisition of the pump-probe measurements that can be used for properly processing 2D data. The final 2D spectrum contains two frequency axes in which the excitation of a molecular transition along one axis, $\omega_{12}$, can be correlated with an emission along the other dimension, $\omega_{34}$. Therefore, well defined phase relationships between the first two interactions and between the third and fourth interaction are required to properly retrieve molecular information. Acquisition of spectra by this method requires a large degree of post processing or "phasing" after collection.

There is a continuing need, however, for improvements in the measurement of two dimensional spectra.

SUMMARY OF THE INVENTION

The present invention relates to systems and methods for multidimensional spectroscopy which involves fewer individual pulse interactions to provide interferometric spectral measurements. In a preferred embodiment, a collinear pulse pair pump and probe system are utilized to provide heterodyned multidimensional spectral measurements. Unlike typical 2D FT measurements in which the first two interactions are spatially separated, in a preferred embodiment the pulse pair is collinear and indistinguishable with respect to time ordering. This symmetry allows for a well defined phase relationship in the signal. Additionally, in this method, the probe field not only acts as an excitation field but also intrinsically heterodynes the signal field. This self-heterodyne removes the need for controlling the phase between the third and fourth interaction since it is derived from the same laser pulse. In a preferred embodiment, because this timing cannot be controlled, spectral interferometry can be implemented to retrieve the proper phase and amplitude information providing identical information to the real part of the 2D measurement performed in the representation known as the "boxcar" geometry.

In the boxcar geometry, to construct a 2D surface, both the rephasing and non-rephasing molecular response pathways are independently taken. The separation of these molecular responses arises from a time ordering and incident direction of the first two impinging pulses. To construct the absorptive (full) 2D surface, absolute time zero for both the $\tau_1$ and $\tau_3$ periods need to be well defined and the relative timing between rephasing and non-rephasing, or absorptive and dispersive, responses in $\tau_1$. This creates three unknowns that can be constrained by an approximation that the projection of the 2D surface is equivalent to the dispersed pump-probe.

For the two-dimensional Fourier transform spectrometer in accordance with the present invention, only three laser pulses need to be used. The third and forth interactions with the sample come from the same pulse removing the $\tau_3$ timing error. Secondly, the rephasing and nonrephasing signals are collected simultaneously due to the indistinguishability of the first pulses. This removes the need for relative timings between this data. Therefore, the only remaining unknown is the absolute time zero in $\tau_1$ which is constrained by fitting the 2D projection to the dispersed pump probe. This geometry removes ambiguity and subjectivity of collecting an absorptive 2D spectrum.

A preferred embodiment can include optical delay elements in the three beams used to probe the medium being measured. Actuators are used to move stages on which the optical delay elements are adjusted. The actuators receive control signals from a stage controller and computer system for precise scanning across a selected delay scan. The system can also include both course and fine delay elements. The delay elements can be retroreflectors or materials of variable thickness or wedges that can be scanned across the beam.

In addition, $\tau_1$ can be measured through an interferometric autocorrelation and by symmetric scanning of the first and second pulses. This provides a much more accurate determination of time zero.

DESCRIPTION OF THE DRAWINGS

FIG. 2B illustrates the timing and spatial relationships between the beams.

FIG. 2C shows a data acquisition and control system of a preferred embodiment of the invention.

FIG. 3 illustrates a light source system in accordance with a preferred embodiment of the invention.

FIGS. 10A-10F show ZZZZ and ZZYY Amide I'-II' 2D IR spectra of poly-L-lysine as a function of pH and temperature of preparation. The β-sheet configuration is shown in FIGS. 10A and 10B (pH=12, T=46° C.); the α helix configuration is shown in FIGS. 10C and 10D (pH=12, T<20° C.); and the random coil configuration is shown in FIGS. 10E and 10F (pH=4, T=20° C.) forms. Contours are plotted from +/−80% of the amide I' normalized peak at a 5% spacing. For the 13-sheet conformation, contours are plotted at 1.25% between +/−20%.

FIGS. 12A-12F show calculated 2D IR spectra for idealized β sheet (FIGS. 12A, 12B), α helix (FIGS. 12C, 12D), and random coil (FIGS. 12E, 12F) secondary structure.

FIGS. 13A-13D show Amide II' β-sheet (FIGS. 13A, 13B) and α-helix (FIGS. 13C, 13D) doorway modes of idealized systems. The visualization map has hydrogen-bonded oscillators (n and n+3 for the α helix) aligned vertically. Below the visualization is the relationship of the II' transition dipole (eigenstates) relative to the secondary structure axis. Coordinate arrows represent the direction of residue addition.

FIGS. 14A-14F include ZZYY 2D IR spectra of ubiquitin at pH=7. (FIGS. 14A and 14B) and at pH=9 (FIG. 14D) and under partial exchange conditions (5° c.); and FTIR kinetic traces of ubiquitin at pH=7 (FIG. 14C) and at pH=9 (FIG. 14F) at 30° c.

FIGS. 15A-15F graphically illustrate the projection along $\omega_1$ axis of ZZYY 2D IR spectra of ubiquitan at pH=1 (FIGS. 15A, 15C and 15E) and ph=9 (FIGS. 15B, 15D and 15F) under partial exchange (dotted line) at 5° c. and after full exchange (heated to 80° c. and cooled to 5° c. The changes to the projection of the amide II diagonal (FIGS. 15A and 15B) and amide II and amide I/I'-II' downward cross peak (FIGS. 15C and 15D) show increase in β-sheet structure; FIGS. 15E and 15F are projection of the amide I' diagonal (ph=1) and amide I/I'-II' upward cross peak (x) and amide I/I'-II' upward cross peak (RC) show partially exchanged secondary structure.

FIG. 16E: FTIR and 2DIR spectrum of ribonuclease A exhibiting the tyrosine absorption at 1515 cm$^{-1}$. FIGS. 16F and 16G FTIR and 2D IR spectra of ubiquitin (FIG. 16F) and Lysozyme (FIG. 16G) that show the symmetric and asymmetric stretch of the guanidyl group of the arginine side chain.

DETAILED DESCRIPTION OF THE INVENTION

The present invention relates to systems and methods of spectroscopy in which a plurality of dimensions can be generated to provide for the measurement of molecular structure and dynamics. General systems and methods for such spectroscopic methods can be found in Khalil et al, "Coherent 2D IR Spectroscopy: Molecular Structure and Dynamics in Solution", J. Phys. Chem. A, Vol. 107, No. 27, 5258-5279 (2003), incorporated herein by reference.

Figure 1:
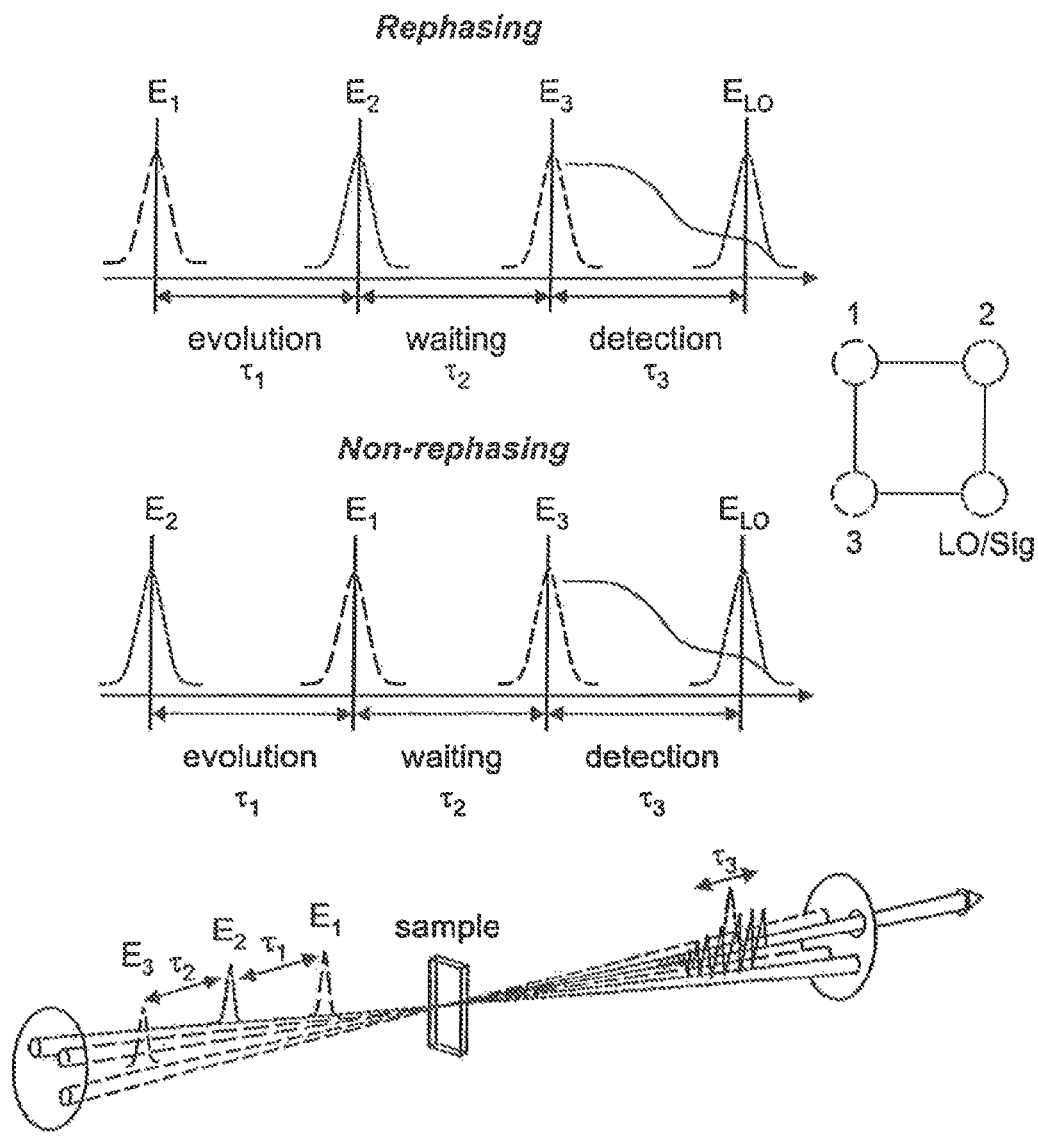
FIG. 1 schematically illustrates the prior art boxcar geometry.
Figure 2A:
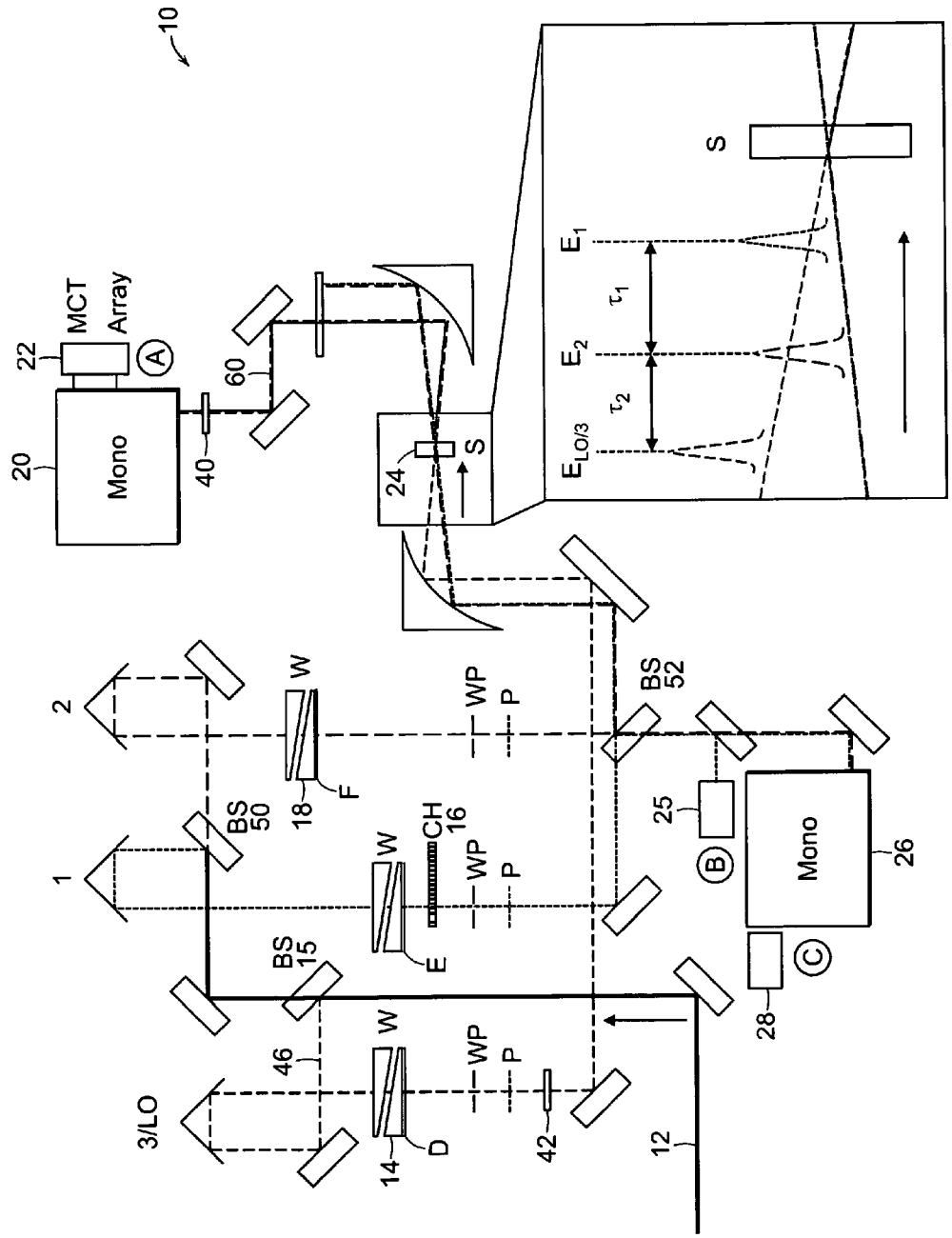
FIG. 2A is a schematic illustration of a multidimensional spectrometer in accordance with the invention.
Figure 4B:
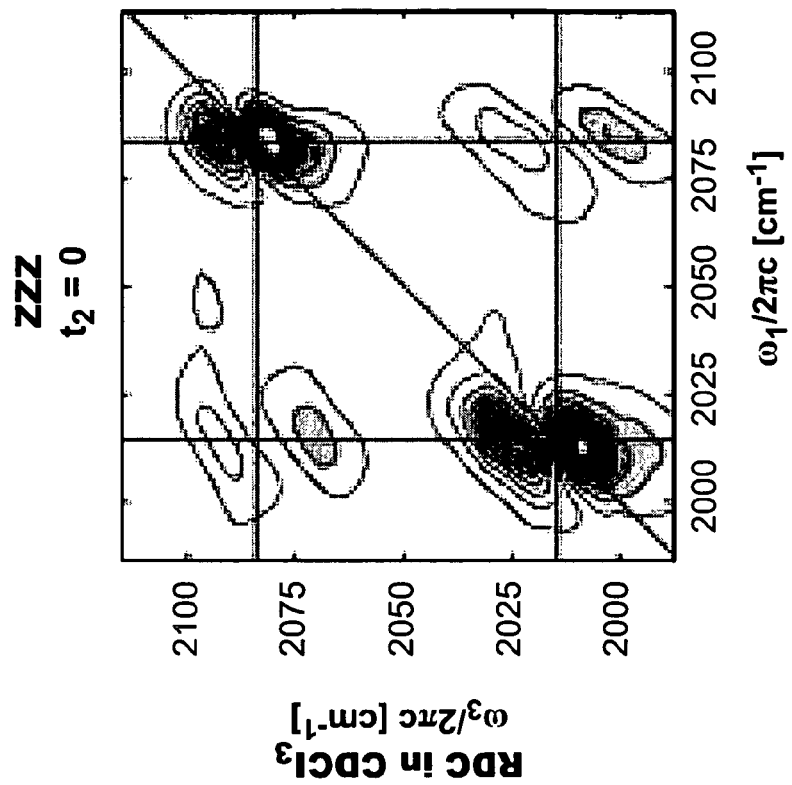
FIGS. 4A-4J are two-dimensional spectra acquired using the systems and methods of the invention.
Figure 4A:
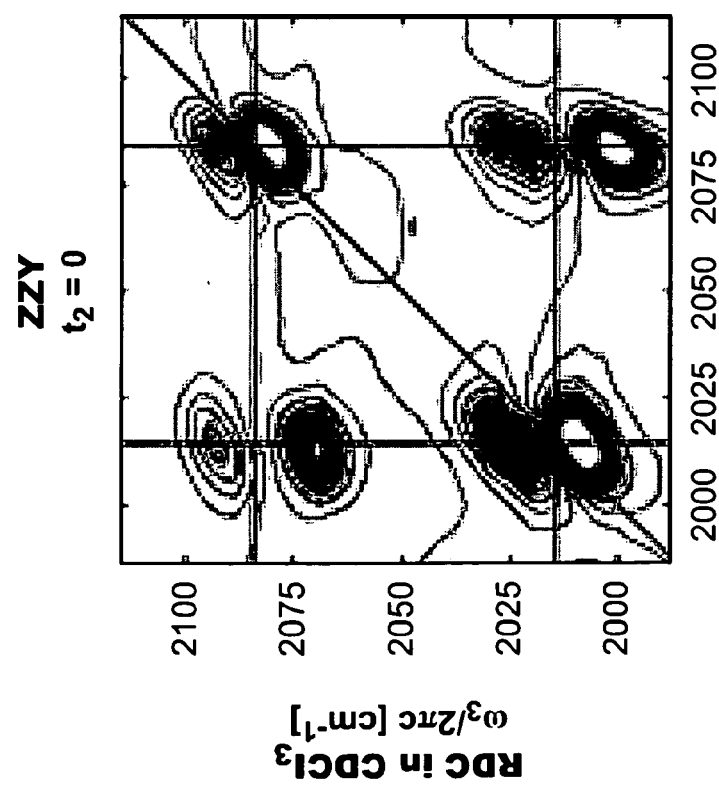
Figure 4D:
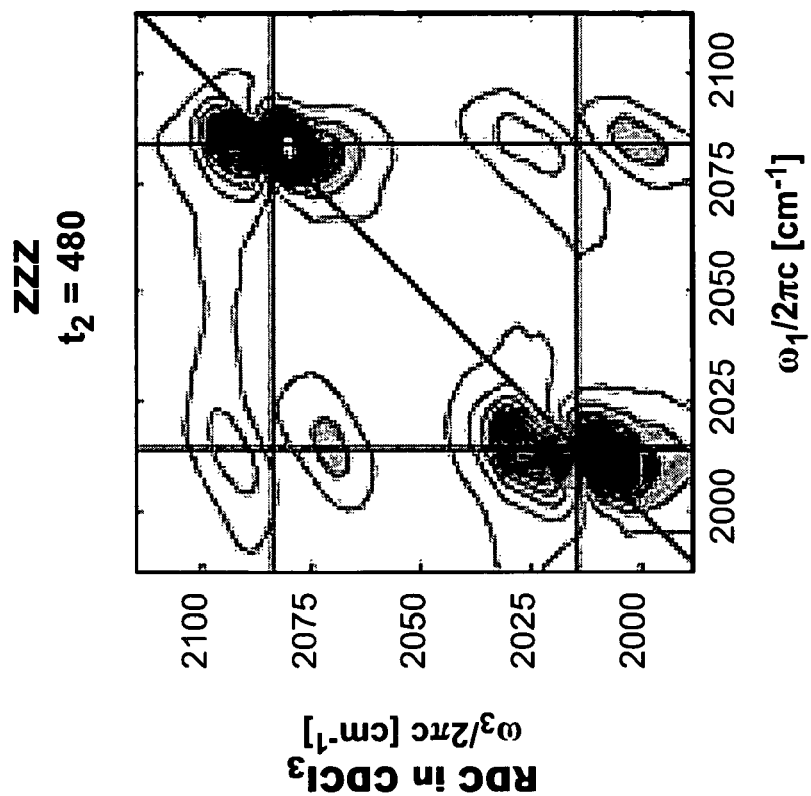
Figure 4C:
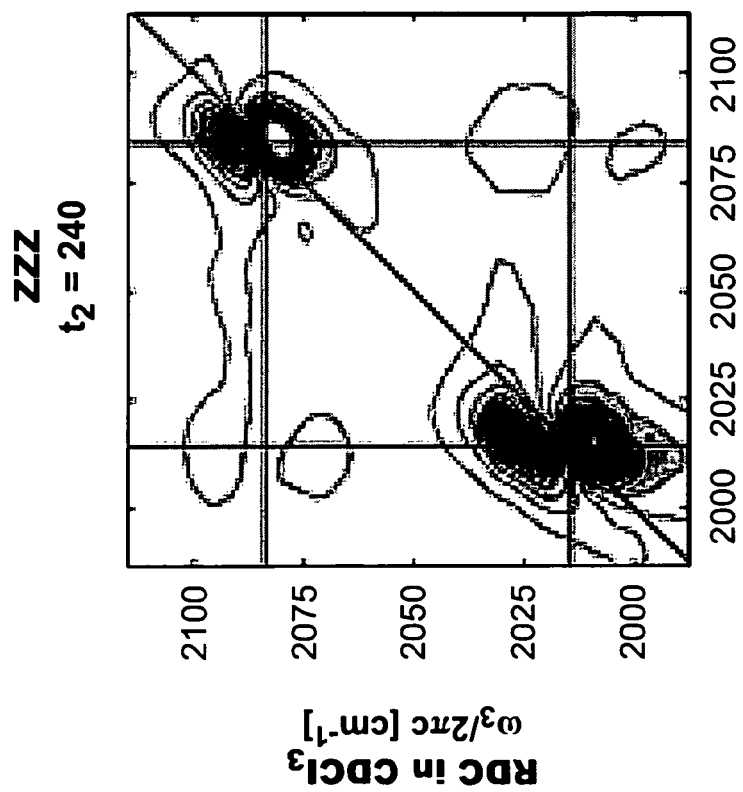
Figure 4F:
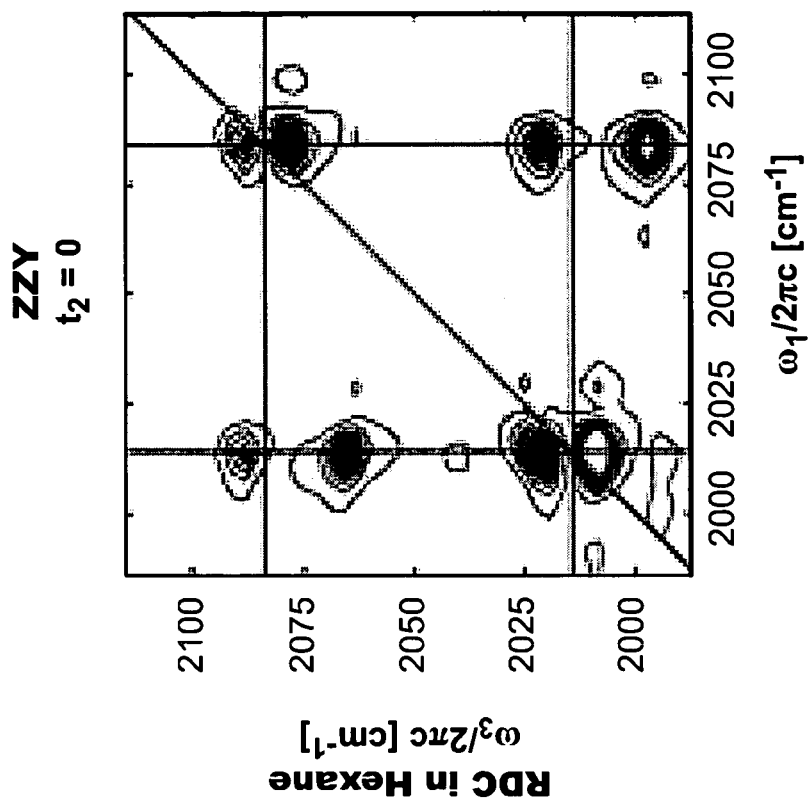
Figure 4E:
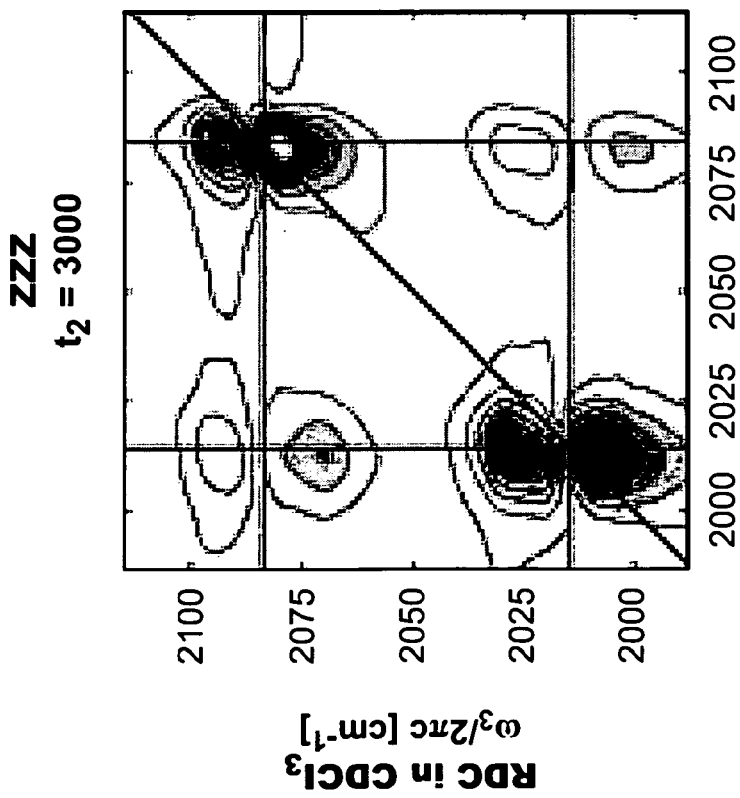
Figure 4H:
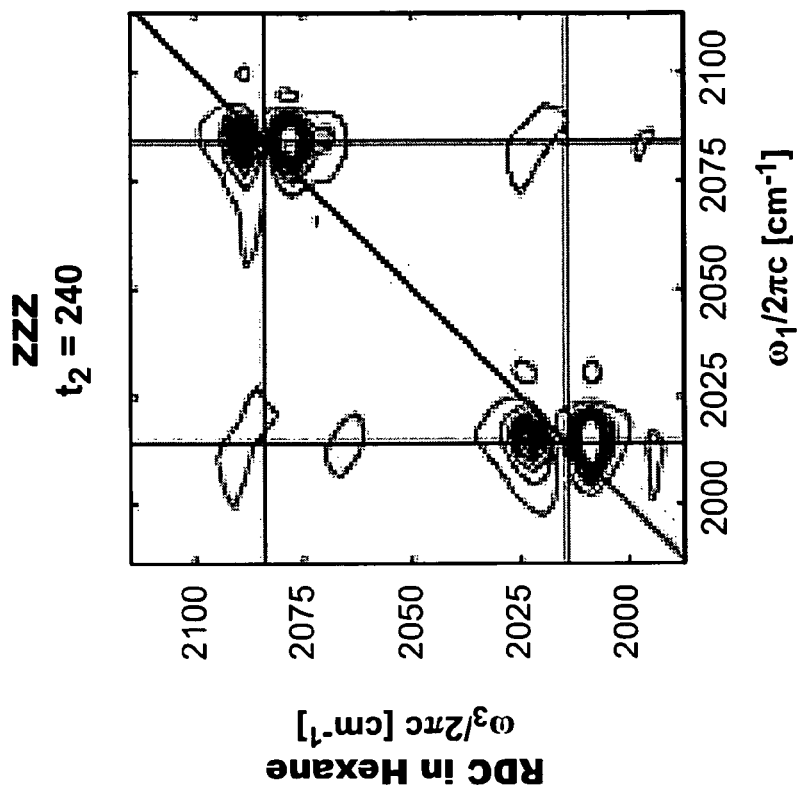
Figure 4G:
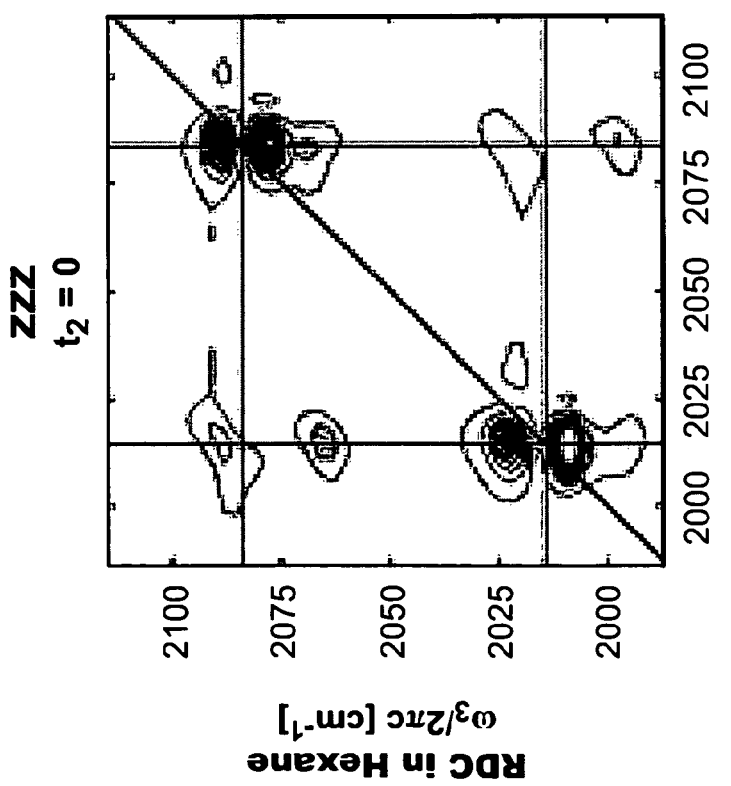
Figure 4J:
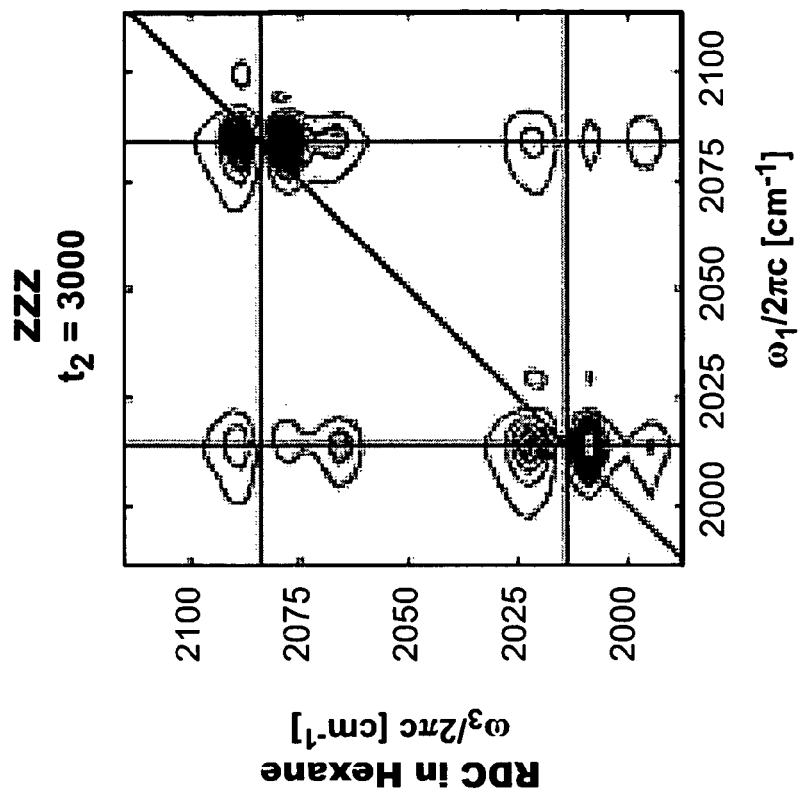
Figure 4I:
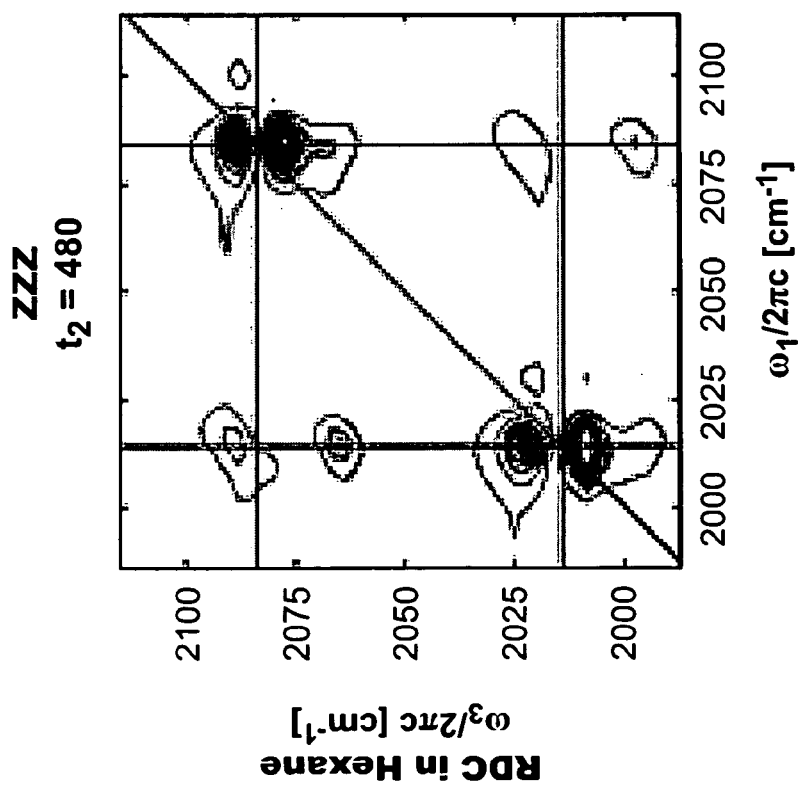

FIG. 2A shows a preferred embodiment of the two dimensional infrared spectrometer 10. The laser system 100 used to generate the infrared pulses can include an amplified Ti:Sapphire (650 μJ, 40 fs, 800 nm, 1 kHz) pumping an optical parametric amplifier 106. A detailed view of the light source system 100 is shown in FIG. 3. The optical parametric amplifier 106 uses a Difference Frequency Generation (DFG) stage for down conversion into the infrared. (4880 nm, 1 kHz, 8 uJ, 80 fs). Two 532 nm pump lasers 120, 122 with 3 W and 10 W of power, respectively, are used for amplification. The laser 122 is a pulsed laser system used for the amplification of the seed 800 nm pulse generated by the oscillator 102. Before the seed can be amplified, the pulse is temporally stretched 104 to reduce damage in the amplification stage 112 and then compressed 108 afterwards. The 800 nm signal is aligned through multi-stage down conversion process in the OPA. To properly align the IR signal through the 2D FT spectrometer 110, the IR signal is overlapped with a visible beam in the IR/Vis overlap box 140. An interface control 110 is used to control operation of the system and can be linked to computer 406 (FIG. 2C).

For the single color 2D FT spectrometer, an incident beam is separated into 2 beams on a beam splitter 15. The reflection 46 is used as the probe (beam 3 and LO) of the 2D measurement. It is sent through a retro-reflector for rough timings to be determined. Fine time control is determined by a computer controlled wedge (W) pair made of ZnSe (Zinc Selenide) on stages 14, 16, 18, under computer control with controller 402 through connections (D, E, F) as shown in FIG. 2C. This material is chosen to minimize temporal broadening in the IR. Alternatively, retro-reflectors are commonly put on computer controlled stages to control pulse timings. The transmitted component of the first beam splitter is separated again into beams 1 and 2 on a second beam splitter 50. Both beams have course timings controlled by a retroreflector and fine timings controlled by wedge pairs. The beams pass through a wave plate (WP) and polarizer (P) to control pulse polarization and intensity. Beam 1 is chopped at 500 Hz using a chopping wheel (CH). This allows for sequential subtraction of laser pulses to improve detection sensitivity. Beams 1 and 2 are combined onto a third beam splitter 52. One pair is used for the 2D measurement and the other is used for determination of time zero and for stage calibration.

Time zero is determined by an interferometric autocorrelation by taking a small reflection of co-propagating laser pulses and focusing them onto a second detector 25 such as a single channel detector. The remaining part is imaged into a monochromator 26 which spectrally selects a single wavelength for detection by a third detector 28. Both are collected as a function of beam 1 delay.

Autocorrelation is a common technique used for measuring the pulse duration and absolute timing of ultra short laser pulses. Two laser pulses are overlapped in space and the time between the pulses is scanned. When the pulse fields are overlapped in time, the light fields interfere (constructive and destructive interference) and a modulation of the signal is seen on the detector. This modulation is collected as a function of delay between the laser pulses. The point of highest modulation defines absolute zero or the point of symmetry. Symmetry arises from the symmetric scan of the pulses with respect to time, the signal is symmetric around time zero. In a preferred embodiment, interferometric autocorrelation is used to measure the time between beam 1 and beam 2. The beamsplitter 52 in which beam 1 and beam 2 are combined before entering the medium or sample 24 creates two replica pulse pairs, which are 180 degrees out of phase. One pulse pair is used for the 2D measurement and the second is used for stage position and calibration.

2D FT surfaces are taken by crossing the pulse pair (beams 1 and 2) and beam 3 through a sample 24 (S). The molecular response is measured by changes to beam 3 as a function of beam 1 delay. Waiting time measurements are performed by controlling the time delay between the pulse pair and beam 3 by moving beam 3 to arrive later at the sample, giving $\tau_2$. The modulated beam 60 is picked off and imaged into a monochromator 20 having a dispersive element, such as a prism or grating, and detected with a multi-channel array detector 22. Each pixel of the array measures a different frequency of light. The signal from the array detector 22 is acquired through the array acquisition board 404 and simultaneously the interferometric autocorrelation and stage calibration data are also acquired. At each time point, the stage position is recorded. The 2D surface is acquired as a function of frequency and time. The stage calibration and interferometric autocorrelation are recorded as a function of time. Once data is collected, it is processed in the sequence described hereinafter.

Spectral interferometry of the remaining IR pulse pair can be collected by imaging through a monochromator 26, centered at 2050 $cm^{-1}$ with a resolution of 1 $cm^{-1}$, onto a single channel MCT detector 28. Spectral interferometry allows the precise stage positions to be determined. This is a required feature when the measurement is performed with common retro-reflection stages rather than the optical delay lines shown here. Alternatively, the monochromator can be replaced by a band pass filter to minimize cost and size of the measurement. These additional elements and the intrinsic nature of the optical system and beam geometry allow for real time data acquisition and control over pulse timings and phase relationships, which to this point, have been one of the major obstacles of 2D IR spectroscopy.

To collect the imaginary part of a 2D surface, the phase of the third field must be controlled relative to the pulse pair. It was previously thought that this could not be done in a geometry other than the "boxcar" technique. However, in transient birefringence and dichroism measurements, the dispersive component can be collected. By introduction of a quarter waveplate 42 into the path of beam 3, as shown in FIG. 2A, the probe pulse can be circularly polarized. This allows for varying phase relationship to be established between the beams, which can be selected out using an analyzer 40 before the detector. To collect the dispersive component, the analyzer 40 can be placed 45 degrees with respect to the polarization of the pulse pair and 90 degrees with respect to beam 3 before the quarter waveplate.

The input infrared laser is centered at 2050 $cm^{-1}$ with a <90 fs pulse duration and 8 µJ of energy. The IR source is split into 3 beams using 50/50 potassium bromide beam splitters (BS) and the pulse pair pump is created by combining beams 1 and 2 onto a third BS as described above. The pulses can have optically controlled time delays made from the ZnSe wedges (W) giving time step accuracy 0.01 fS/µm and a wave-plate/polarizer (WP/P) pair for controlling polarization and pulse intensity. The pulse pair (beams 1 and 2) and the probe (beam 3/LO) are focused into the sample with a spot size of 150 µm. The signal is generated in the phase matched direction which propagates along the transmitted probe beam. Beam 3, also intrinsically heterodynes the generated signal. To detect the 2D spectrum, the probe beam 60 is collimated and spectrally dispersed using a monochromator and imaged onto a 64 channel MCT array. Spectral interferometry is a preferred element for this method as discussed above. The 2D spectrum is collected as a function of delay between the pulse pair. To remove the contribution of other phase matched signals, beam 2 is chopped (CH) at 500 Hz and consecutive shots are subtracted. The pulse pair time delay is generated by stepping or scanning stage 16 for beam 1 relative to the other pulses. The scanning method allows for rapid acquisition of 2D spectra at a rate of ~1 ps delay/15 seconds.

In FIGS. 4A-4J show 2D IR spectra of a metal carbonyl, rhodium di-carbonyl (RDC), in two different solvents, deuterated chloroform and hexane using this method. It is important to note that this method provides identical information to the absorptive 2D spectra generated from the more common "boxcar" technique. By comparing the 2D spectra of a molecular in different solvents, the degree of homogeneity in these systems can be seen. The peak structure of RDC in hexane is narrow and symmetric while RDC in CDCh is diagonally elongated indicative of inhomogeneous broadening. In addition, the appearance of off-diagonal peaks, arising from vibrational coupling, is seen in all these spectra. These are two of the salient features that prove the usefulness of this method. This demonstrates the capability of acquiring polarization sensitive 2D spectra to provide information about dipole orientation and molecular structure. This is seen by comparison of the off diagonal resonance intensities in the ZZY and ZZZ $\tau_2$=O surfaces. Note ZZZ and ZZY refer to the polarization of beams 1,2,3. The relative increase in intensity of the ZZY cross peaks arise from the 90 degree angle between the transition dipole moments of the symmetric and asymmetric modes of the RDC molecule. Spectra reflecting molecular dynamics and relaxation are acquired by controlling the time delay between the pulse pair and the probe beam. In FIGS. 4B-4E and 4G-J, waiting times of 0 fs, 240 fs, 480 fs and 3000 fs in the ZZZ polarization as shown. In this system, energy coherently transfers between the modes in RDC with an oscillation time of 480 fs. By comparing the intensities of the off diagonal peaks in the 240 fs and 480 fs shows the troth and crest of the oscillation. At the waiting time of 3000 fs, the off-diagonal peaks grow in and the diagonal resonances become symmetric, both are important features in a 2D spectrum. Multi-dimensional infrared techniques have gained wider use due to the availability of high power commercial laser systems. However, the complexity of the measurement has limited the accessibility of these techniques to the more general scientific community. Particularly, in the case of high order experiments which rely on multiple pulse interactions and require excessive labor with slow scientific throughput. In these measurement, accurate control of pulse timings and spatial overlap is required. The demonstrated measurement reduces this complexity by implementing fewer laser pulses and including real time acquisition of pulse timings and characteristics. This method employs traditional optical techniques and components thereby improving robustness and reducing cost by reducing the number of pulse and delay lines while simplifying the overall alignment. Despite these simplifications, all the salient details are still present, enabling measurements of molecular couplings, structure and dynamics.

In addition to the aforementioned improvements, traditional measurements require a large degree of post collection data processing in which multiple spectra, collected by moving different stages, have to be stitched together to acquire the desired absorptive spectrum. Uncertainty in pulse timings and absolute zero complicate this process. Implementation of the interferometric autocorrelation and stage calibration removes this uncertainty. In addition, the intrinsic nature of this method in which absorptive data is acquired with a single stage removes the need for post data collection processing.

The overall beam geometry in this method, in which the pulse pair pump and probe are crossed in the sample, reduces alignment difficulty. Due to the natural phase matching in this geometry, multi-color experiments, that probe spectrally separated molecular transitions, can be performed by simply altering the input laser field or replacing the input laser with a broad band (continuum) light source. In the traditional technique, the 4 beam boxcar geometry must be drastically modified for a multi-color measurement, which is due to the wavelength dependence of the vector matching condition. In contrast, the system of the present invention is more versatile for general application, and opens the opportunity for use with commercial spectrometers. With this, these measurements can also be integrated with off-the-shelf commercial Fourier transform infrared spectrometers (FTIRs), making it suitable as an add-on.

There are a number of applications for multi-dimensional infrared spectroscopy to be used as a diagnostic instrument from biology to materials. For biomedical this can include structural determination, rapid screening and, in the case of proteins, folding dynamics. For biochemical systems, enzyme activity seen through coupling of vibrations can be determined. This technique can be used for the visible and far-infrared as well as multi-color experiments.

Additional embodiments can be made for single color applications in the UV, optical, infrared and Terahertz regions. This requires different optical coatings on beam splitters and mirrors and detectors but the overall system can still be used.

Figure 5A:
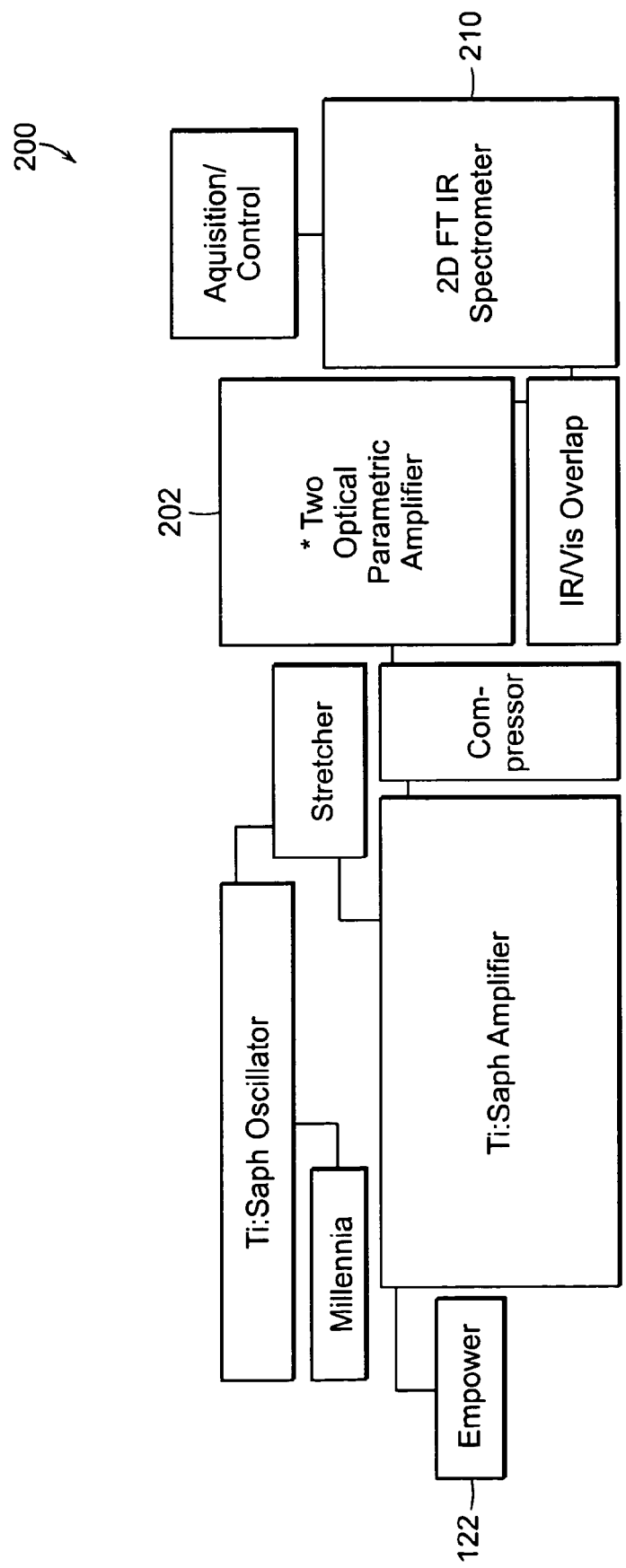
FIG. 5A shows a light source emitting at a plurality of wavelengths for another preferred embodiment of the invention.
Figure 5B:
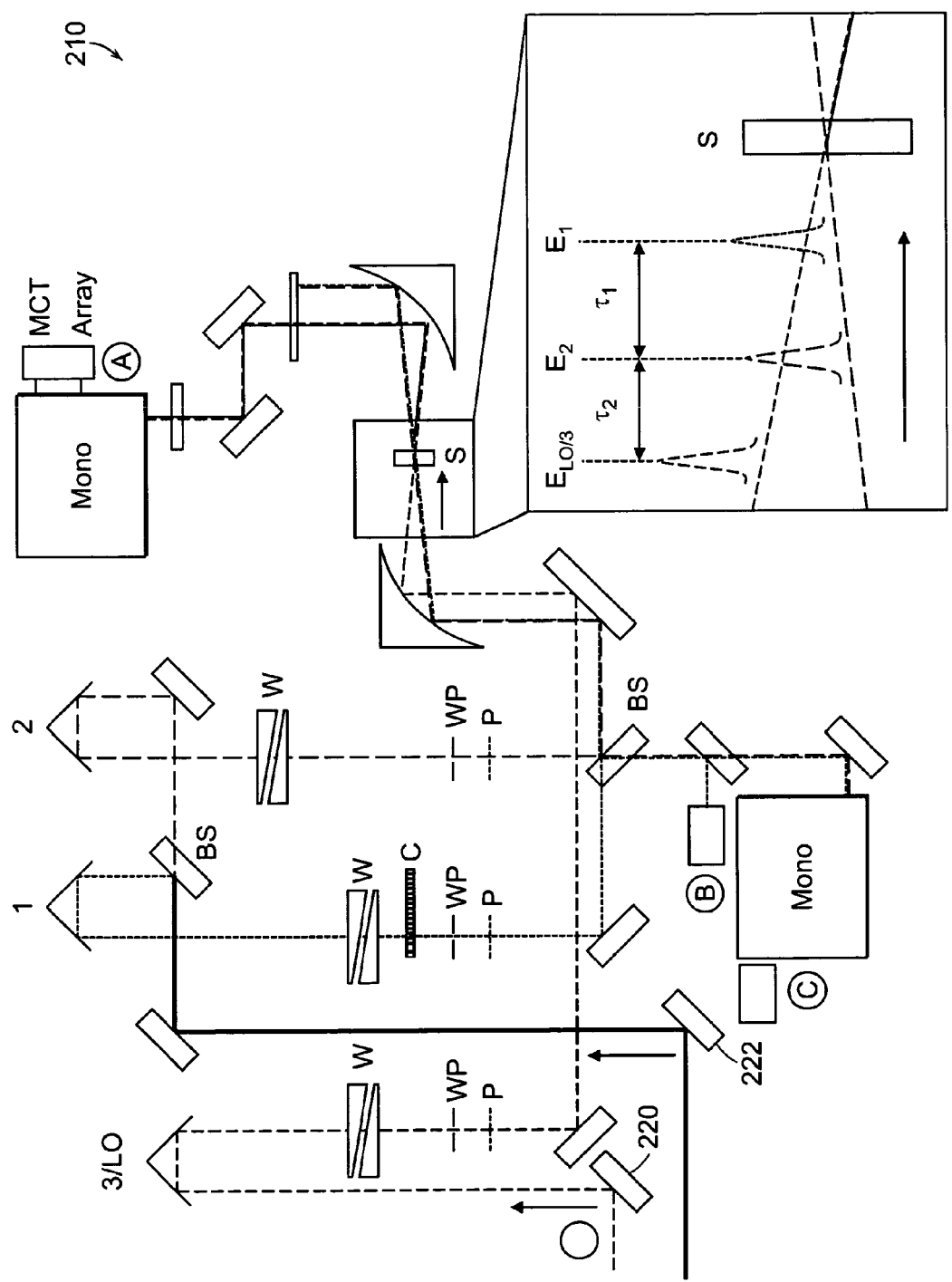
FIG. 5B illustrates a spectrometer for measuring a 2D spectrum using a plurality of wavelengths.

Another embodiment for multi-color and broadband measurements requires certain modifications to the system. Modifications include the use of multiple optical parametric amplifiers 202 for generation of different wavelengths as shown in FIG. 5A. In the spectrometer 210 initial beam splitter is no longer required before as the second color is now used as the probe (or beams 3 and LO). The rest of the system 200 remains identical, as will acquisition of the 2D surface and stage positioning. Due to the nature of the measurement in which there is no need for phase matching (i.e. beam 1 and 2 are co-propagating), two color and broadband measurements are intrinsically phased matched. As shown in FIG. 5B, the two light sources are coupled to the spectrometer at mirrors 220, 222.

Figure 6B:
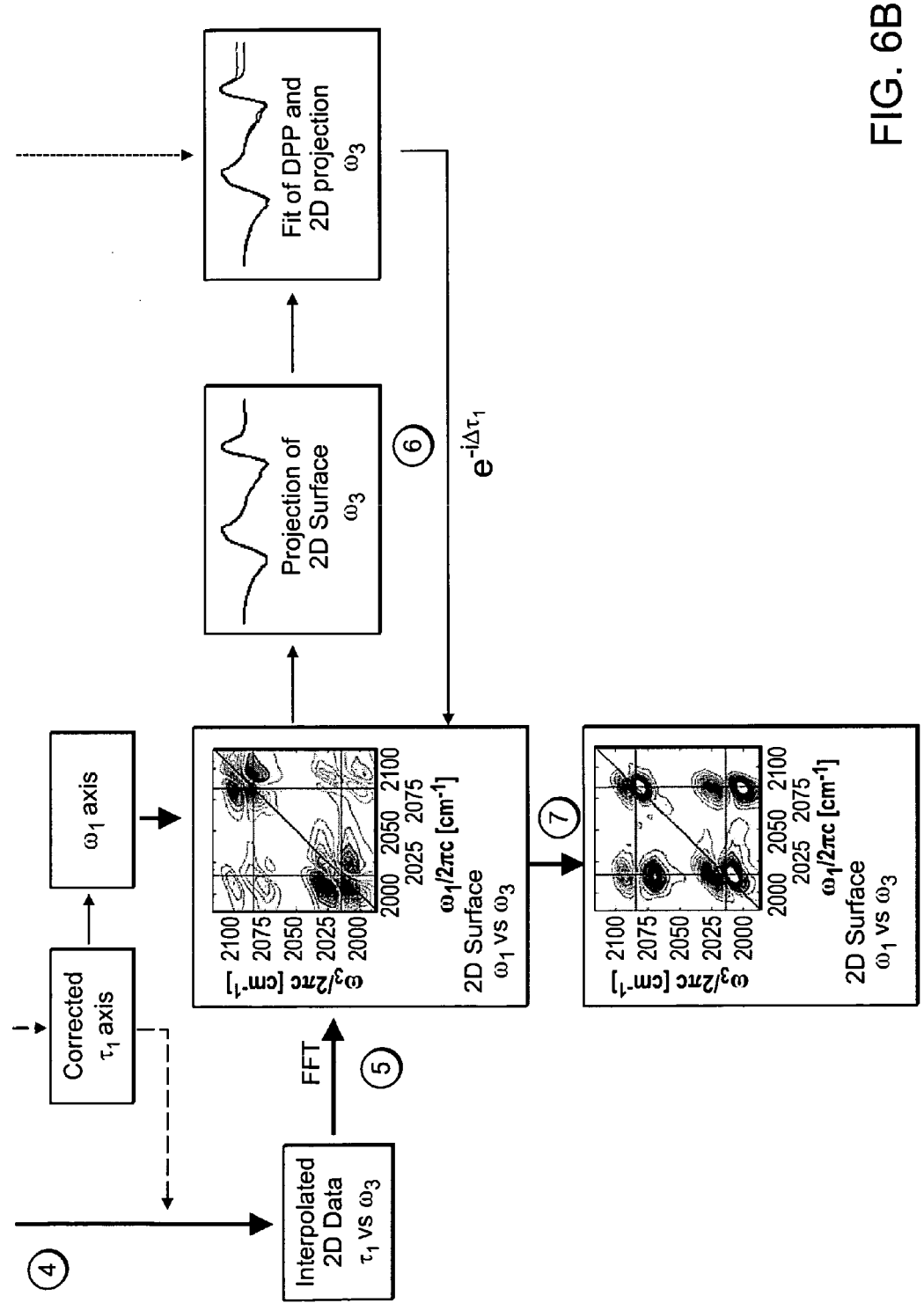
FIG. 6 illustrates a process sequence for collecting 2D spectra in accordance with preferred embodiments of the invention.

Data is collected and processed by a computer using programmed software as shown in FIG. 6. (1) In real time, the 2D surface data, time position, stage calibration and interferometric autocorrelation is acquired. (2) In a separate measurement, by simply blocking beam 1, the dispersed pump-probe is collected. In this measurement, the first 2 interactions are derived from pulse 2 unlike the 2D measurement where the pulse interactions are derived from temporally independent pulses. (3) The stage calibration is determined by performing a fast Fourier transform (FFT) of the stage calibration trace as a function of $\tau_1$. The frequency of the transformed trace is compared with the position of the monochromator to determine the overall stage calibration. In addition, for use of retro-reflectors which require much more accurate stage positions, the phase can be extracted from the stage calibration and the exact error in every stage position is determined. The individual and overall stage corrections are applied to the original time axis, as is the absolute time zero correction determined by the interferometric autocorrelation. Since an interferometric autocorrelation is symmetric in time, the symmetry point of this interference defines time zero. This correction is applied the $\tau_1$ axis and a new axis is made. (4) The raw 2D data is interpolated onto the new time axis and (5) a FFT is performed to acquire the frequency-frequency 2D surface. The $\omega_3$ frequency axis is determined from the corrected time axis. The $\omega_3$ axis is determined from calibration of the array through spectral interferometry. This is performed independent of the actual experiment. (6) Once the frequency-frequency surface is obtained, the surface is projected onto the $\omega_3$ axis and compared to the dispersed pump-probe. The surface is corrected by iterating a phase factor along $\omega_1$ that is proportional to the error in absolute timing of $\tau_1$. This factor is multiplied by the transformed data and the fit is iterated to minimize the difference using a least squares method. Once the fit is determined, the final 2D surface is acquired.

Figures 2, 7A:
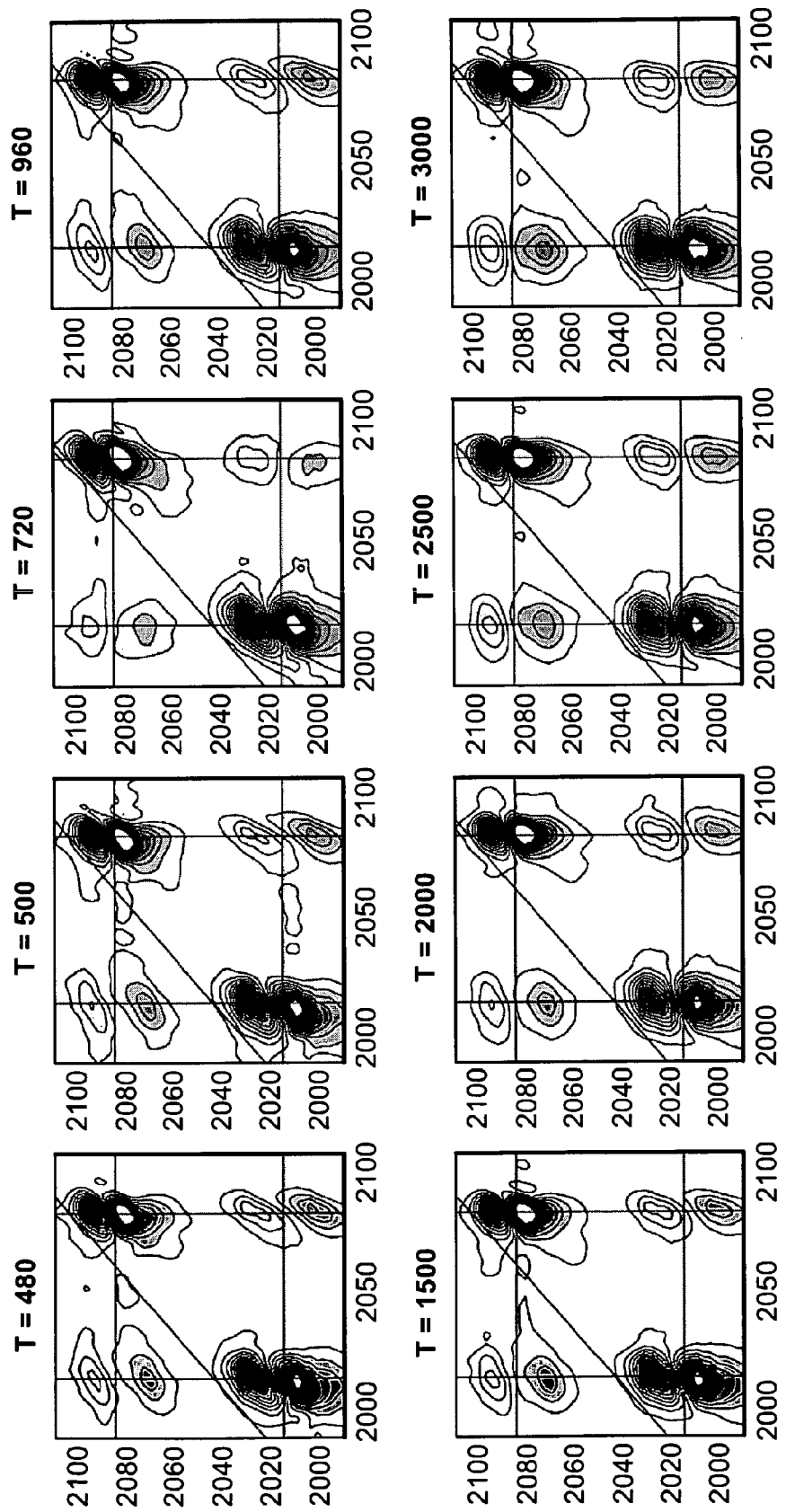
FIGS. 7A-7E illustrate 2D spectra acquired in accordance with the invention.
Figure 7B:
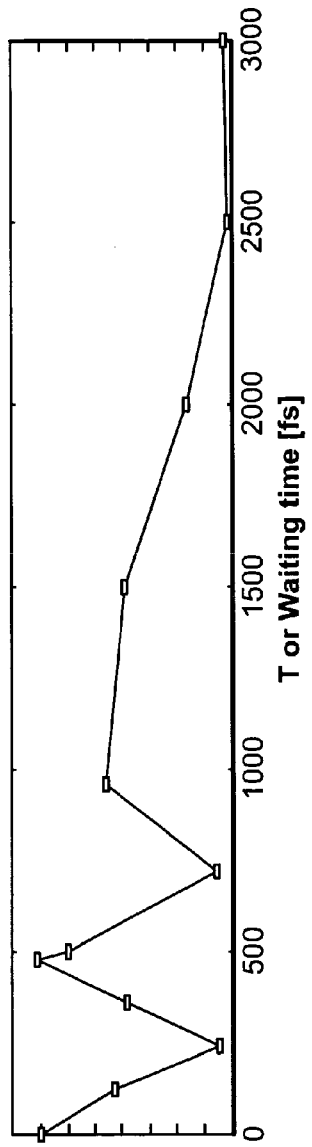
Figure 7C:
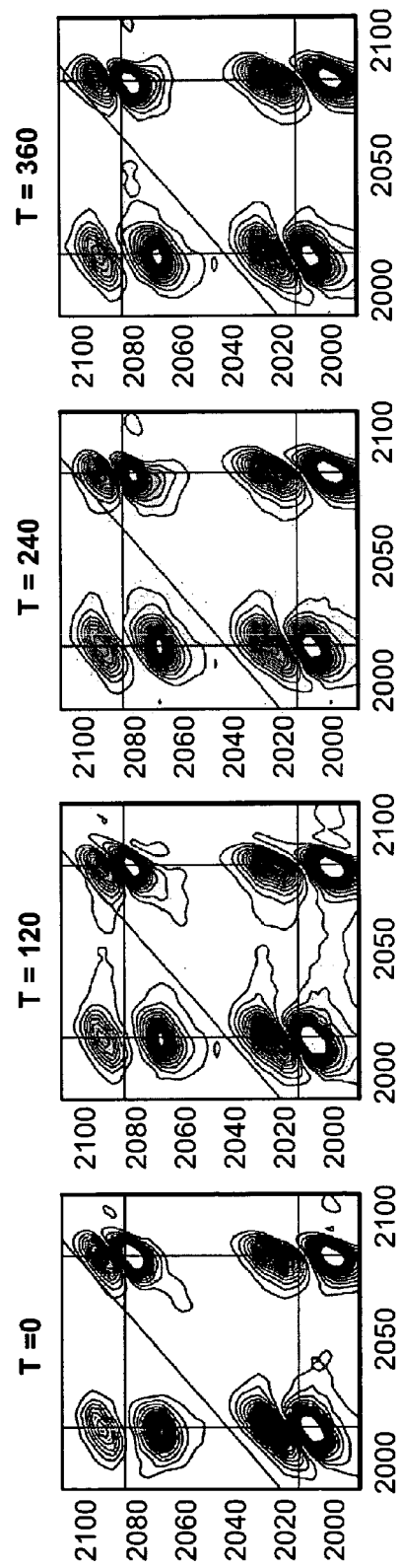
Figures 2, 7C:
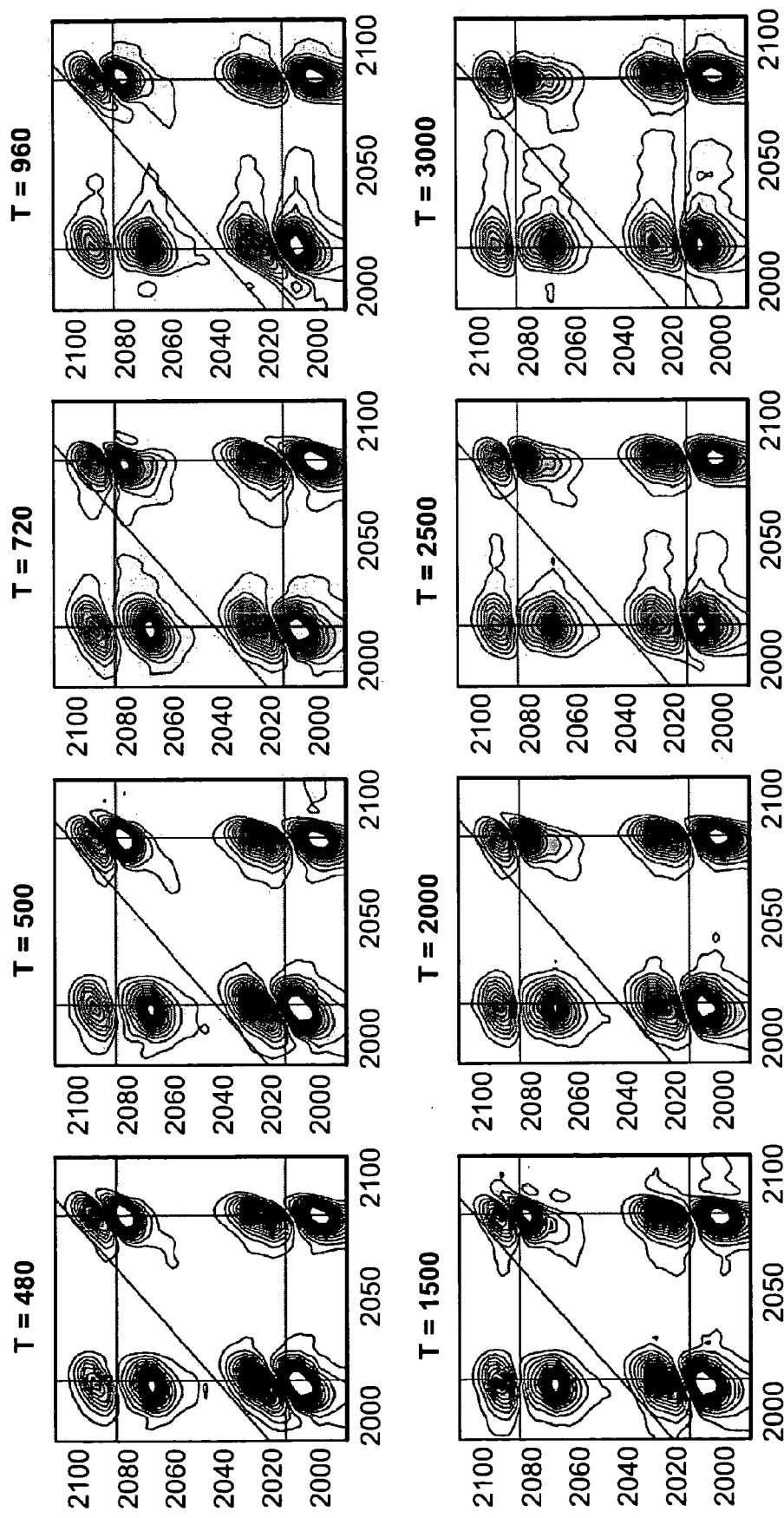
Figures 2, 7D:
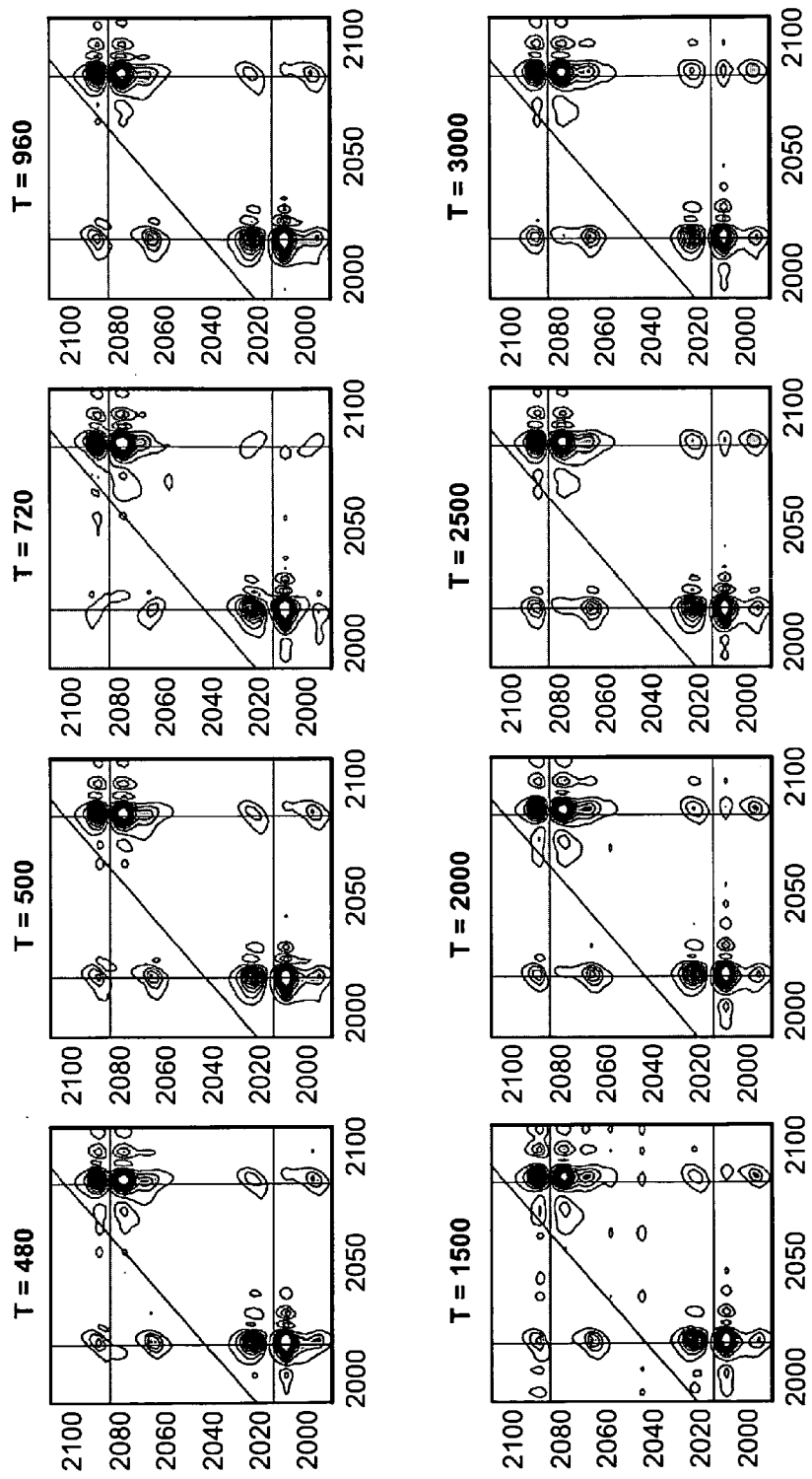
Figures 2, 7E:
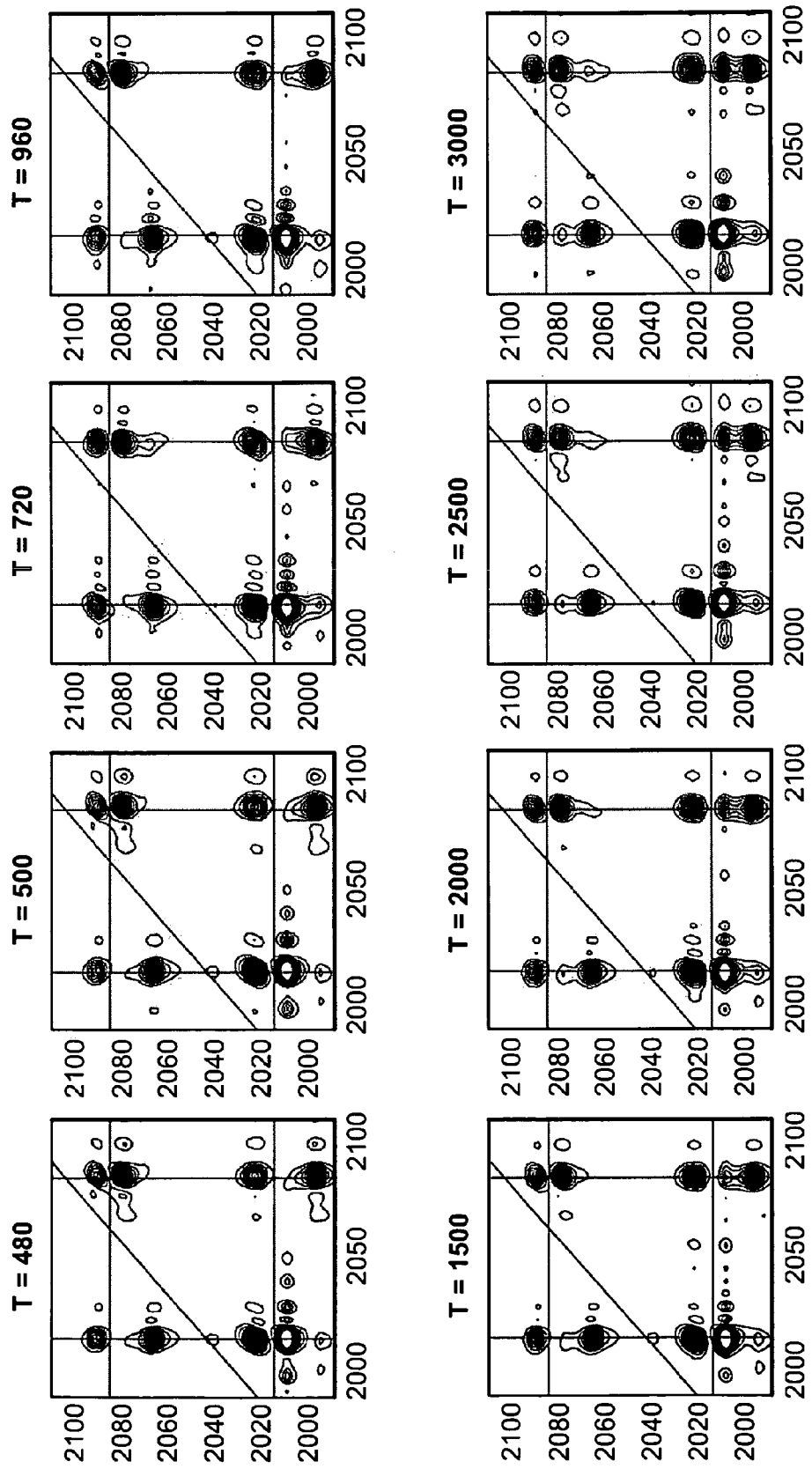

FIGS. 7A-7E illustrate spectral data measured using systems and methods in accordance with the invention. In FIG. 7A, the ZZZZ waiting time series of RDC in chloroform. The integrated cross peak region circled in FIG. 7A is displayed as a function of waiting time in FIG. 7B. The ZZYY waiting time series of RDC in chloroform is shown in FIG. 7C. The ZZZZ waiting time series of RDC in hexane is shown in FIG. 7D. The ZZYY waiting time series of RDC is hexane is shown in FIG. 7E.

Figure 8A:
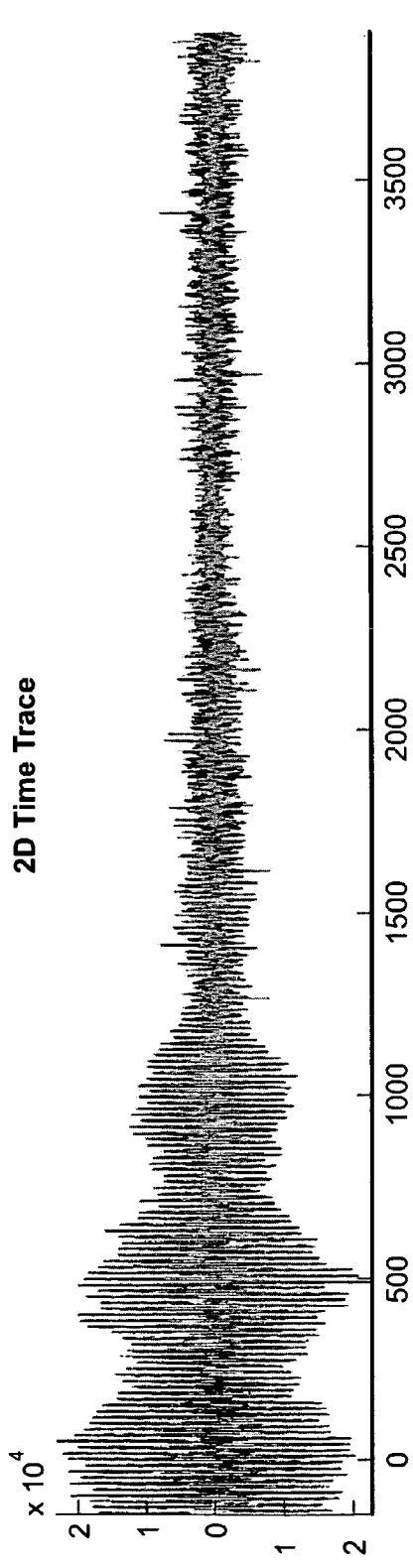
FIGS. 8A-8C illustrate a 2D time data at a selected frequency $\omega_3$, stage calibration data and interferometric autocorrelation data, respectively.
Figure 8B:
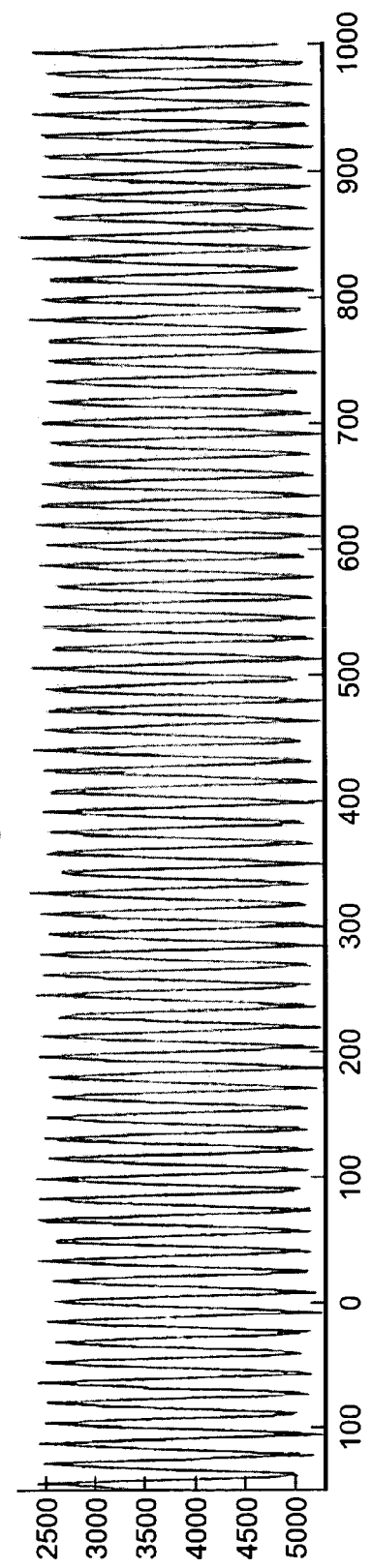
Figure 8C:
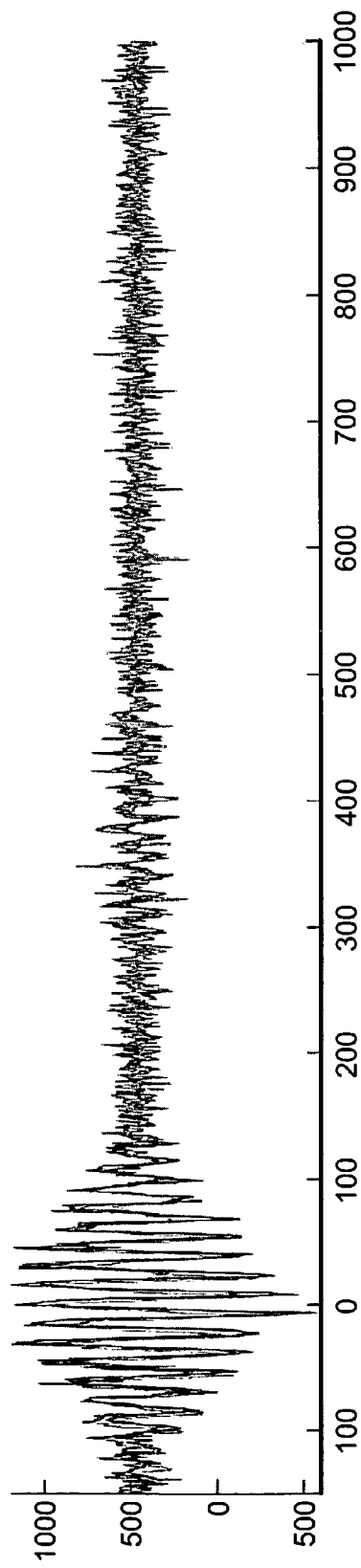

FIGS. 8A-8C illustrate data acquired in accordance with the invention. FIG. 8A is a 2D time trace of spectral data acquired at a specific $\omega_3$ frequency. FIG. 8B shows a data set recorded for stage calibration. FIG. 8C shows an example of interferometric autocorrelation data. These measurements were taken as a function of beam 1 delay.

Another aspect of the invention is the use of the systems and methods described above to characterize the secondary structure of a molecule, such as a polypeptide or protein, situated in the medium that is illuminated. The spectral representation formed during 2D IR spectroscopy can provide information characteristic of protein secondary structure, such as α helix, β sheet, and random coil structure. The relative amounts of each such secondary structure in a sample containing one or more protein molecules, or changes in such structures over time, or in response to an added chemical agent, can be determined by comparing the results to those obtained for either real or calculated reference spectra characteristic of each type of secondary structure.

Using a test polypeptide, multi-mode 2D IR spectroscopy of protein amide I' and amide II' vibrations were shown to provide spectral signatures that distinguish protein secondary structures. Polarization-dependent amide 2D IR experiments on poly-L-lysine in the β-sheet, α-helix, and random coil conformations showed that a combination of amide I' and II' diagonal and cross peaks can effectively distinguish the secondary structural content where traditional amide I' infrared spectroscopy cannot.

The most studied protein vibration, amide I, is composed predominately of peptide carbonyl stretch and displays secondary structure sensitivity. Empirical frequency-structure correlations have found that β-sheets have a strong absorption band at 1610-1640 cm$^{-1}$ and a weaker band at 1680-1690 cm$^{-1}$. The α-helix and random coil structure are located at 1640-1650 cm$^{-1}$ and 1650-1660 cm$^{-1}$, respectively. While anti-parallel β sheets and aggregates give rise to distinct diagnostic amide I bands, other secondary structures are poorly resolved in an amide I line shape with multiple contributions. The α-helical structure is predicted to have three IR active amide I modes, but the peak splitting is on the order of a few cm$^{-1}$ and the features are not resolvable.

The amide II vibration, due to its composition of NH bend and CN stretch, is predominately known for its sensitivity to the protonation or deuteration state of the peptide unit. Its 100 cm$^{-1}$ frequency downshift between protonated (amide II) and deuterated (amide II') states can be used with kinetic H/D exchange experiments to probe water exposure of protein structure. In an oriented film of poly-γ-benzylglutamate that forms extended helices, amide II vibrations appear at 1516 and 1546 cm$^{-1}$, however no clear structure is seen in solvated proteins. For random coils, the amide II vibration absorbs at 1536 cm$^{-1}$ giving a potential signature for differentiating between coils and helices.

2D IR was used to resolve details of the 2D amide II' lineshape and investigate the amide I'-II' cross-peaks in a test system (poly-L-lysine (PLL)) that adopts different secondary structures. 2D IR cross peaks that are used to characterize secondary structure were found to have specific spectral features. The amide II' 2D line shape gives rise to distinctive signatures for α helices and random coil regions, which, when combined with the β sheet sensitivity of the amide I region, allow for separation of all the common secondary structural motifs. Polarization dependent experiments can be used to quantify vibrational couplings and transition dipole orientations between amide II' oscillators and between amide I' and II', and also describe the symmetry of the modes involved. 2D IR spectra can be interpreted using an excitonic representation for the amide I'-II' manifold suitable to predict protein amide I'-II' FTIR and 2D IR spectra.

Samples were held in a temperature-controlled cell with 1-mm thick calcium fluoride windows and a 50 μm path length. Concentrations of the polypeptides were selected such that the infrared absorbance of the amide I band was <0.5. Poly-L-lysine samples were prepared under different conditions in order to generate the desired secondary structure motif. The random coil species was prepared by dissolving the protein in neat D$_2$O at 20° C. and pH=4.0. The α-helical conformation was prepared by dissolving PLL into neat D$_2$O and raising the pH to 12 using 1M NaOD solution. The β-sheet form of PLL was prepared by subsequently raising the temperature of the α-helical solution to 46° C. over 30 minutes. Spectra of the helical and sheet moieties were taken consecutively on identical samples.

2D IR experiments were performed with bandwidth sufficient to cover the fundamental and overtone bands of amide I' and amide II' using a 2D FT spectrometer system as described above. The mid-infrared laser pulse was centered at 1550 cm$^{-1}$ with a FWHM bandwidth of approximately 350 cm$^{-1}$ and compressed to <90 fs in duration. 2D IR spectra were acquired in a two beam geometry using a collinear pulse pair to pump and third pulse to act as probe and local oscillator. The excitation dimension was obtained by step scanning the τ1 time axis to XXX ps in steps of XXX fs giving a resolution of XXX cm$^{-1}$. The transmitted probe was dispersed in a monochromator using a 75-groove/mm grating and collected using a 64 pixel MCT array detector. The 1.9 cm$^{-1}$ resolution in the $\omega_3$ detection axis resulted in a 120 cm$^{-1}$ single-scan detection bandwidth. 2D spectra were assembled from spectrograms centered at 1450 cm$^{-1}$ and 1650 cm$^{-1}$. Fourier transformation of the signal as a function of the timing between pump pulses ($\tau_1$) resolved the 2D spectrum along the $\omega_1$ axis.

Analysis of amide I'-II' spectra drew on idealized structures for an anti-parallel β sheet, α helix, and random coil. The idealized anti-parallel β sheet consisted of six strands with six peptide units per strand. It was generated by repeating φ=−139° and ψ=135° for each strand and spacing the cross-strand groups 3.04 Å apart. A 20 residue α helix was generated by repeating φ=−57° and ψ=−47°, yielding a 1.80 Å separation of hydrogen bonded O-H. Calculations for the random coil involved an average over 5000 snapshots of a molecular dynamics simulation of an 18-oscillator peptide in vacuum at 1000° C.

Amide I'-II' spectra were calculated by diagonalizing a local mode Hamiltonian developed in the basis of the amide I' and II' vibrations for the individual peptide units. The elements of this local amide Hamiltonian were assigned on the basis of the position of the peptide units within the structure. Details of the amide II' Hamiltonian are given below. The amide I vibrations are characterized by anharmonically coupled oscillators with degenerate site energies of 1675 cm$^{-1}$ and anharmonicity of 16 cm$^{-1}$. Using the orientation of the amide I' transition dipole was set 20° off the C=O bond, with the dipole center located 0.868 Å along the carbonyl axis, and a normalized unit dipole strength of 1.0. Non-bonded amide I'-I' interactions were determined through transition dipole coupling, whereas bonded interactions were determined from a DFT map. Two-quantum states were introduced through a weak anharmonicity and harmonic scaling of the transition moments. Spectral calculations involved a sum over transition pathways between eigenstates weighted by polarization factors. Calculations can be averaged over a static disordered system using a homogeneous linewidth (FWHM).

Figure 9:
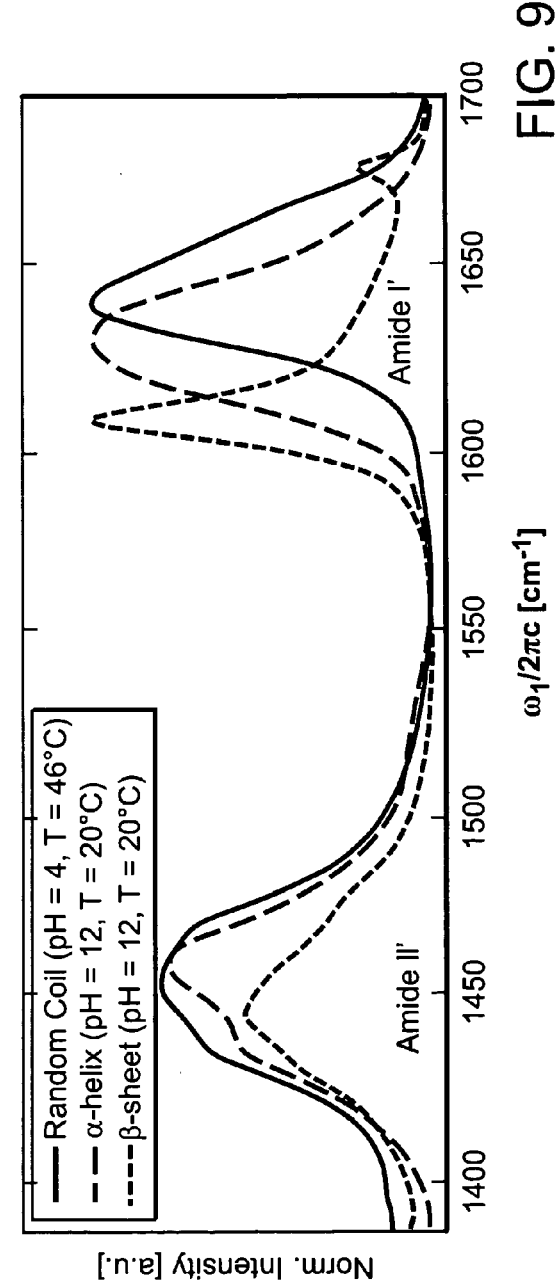
FIG. 9 shows FTIR (Fourier transform infra red) spectra of poly-L-lysine as a function of pH and temperature showing the β-sheet (pH=12, T=46° C.), α-helix (pH=12, T<20° C.) and random coil (pH=4, T=20° C.) forms of the polypeptide.

The FTIR spectra of the three forms of poly-L-lysine are shown in FIG. 9. In random coil form, poly-L-lysine shows a small shoulder on the blue side of the amide I band maximum (1660 cm$^{-1}$), and is broad and suggestive of overlapping resonances in the amide II' band. In the α-helical form, the amide I' band is red-shifted and asymmetric. This lineshape is commonly interpreted as the overlapping contributions from the intense A band near 1640 cm$^{-1}$ ($v_A$) and the weaker blue-shifted E bands ($v_E$). The amide II' band shows a distinct two peak structure. As the temperature of the α-helical form is increased, PLL undergoes a structural transition into a β-sheet aggregate. In β-sheet form, the amide I' band splits into the signature high and low intensity β-sheet modes. The 1610 cm$^{-1}$ and 1690 cm$^{-1}$ modes are termed $v_\perp$ and $v_\parallel$, respectively, to refer to whether the amide I oscillators of the mode vibrate in-phase perpendicular or parallel to the strands of the sheet. For the β sheet, amide II' does not exhibit such a drastic change, but rather loses structure.

The 2D IR spectra of PLL in the various secondary structure conditions are shown in FIG. 10 for parallel (ZZZZ) and perpendicular (ZZYY) polarized probing. Spectral regions of interest include the lineshapes of the amide I' ($\omega_1, \omega_3$=1600-1700 cm$^{-1}$) and II' ($\omega_1, \omega_3$=1400-1500 cm$^{-1}$) diagonal regions, and the amide I'-II' cross peaks. The secondary structural sensitivity was revealed by describing the contours of the 2D lineshapes, which result from interference between positive (fundamental) and negative (overtone) transitions within the amide band. In addition, since the cross peak intensity scales quadratically with the dot product of the diagonal transition dipole moments, it encodes both the magnitude and the relative angle between the transition dipoles. Comparison of the cross peak amplitude as a function of polarization reveals the angle. Qualitatively, the enhancement of a cross peak in crossed polarization indicates a transition dipole projection angle close to orthogonal (>70°), while a decrease indicates angles closer to parallel.

The amide I' region of FIG. 10A shows the characteristic S-peak structure for extended β-sheets, which arises from fundamental and overtone transitions of the $v_\perp$ and $v_\parallel$ vibrations and cross-peaks between them. The amide I'-I' cross peaks are enhanced in the ZZYY spectra in FIG. 10B, and a comparison of ZZZZ and ZZYY spectra gives an angle of 65° between the transition dipoles of the two modes. Similar to amide I', the diagonal amide II' region shows two peaks in the parallel spectrum ($\omega_1, \omega_3 = 1440$ cm$^{-1}$ and 1490 cm$^{-1}$) and an enhancement of the cross peak between them in the perpendicular spectrum.

Figure 11A:
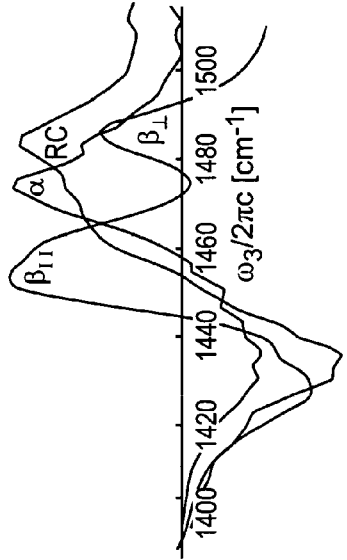
FIGS. 11A-11D compare experimental (FIGS. 11A, 11B) and calculated (FIGS. 11C, 11D) ZZYY 2D IR projections. Projections of the β sheet, α helix, and random coil of the amide II' diagonal (1420-1500 cm$^{-1}$) and the amide I'-II" downward cross peak (1600-1700 cm$^{-1}$). Projections show identical band structures with inclusion of negative nearest neighbor couplings.

The amide I' regions of the α-helix and random coil 2D spectra are similar, and it is difficult to distinguish between the two moieties using only the amide I' mode. The random coil lineshape is more diagonally elongated ($\omega_1 = \omega_3$) than the α helix, which shows slight off-diagonal broadening that hints at the underlying A and E1 helix mode structure. However, examination of the amide II' region of FIGS. 10C and 10E reveals distinct differences; the random coil line shape is again diagonally elongated while the α helix shows two peaks. Surprisingly, both the α helix and random coil show anti-diagonal broadening in the perpendicular spectra. This arises from a plateau ($\omega_3 = 1480$ cm$^{-1}$) indicative of a cross-peak between two modes. A clearer indication of the amide II' structural sensitivity is seen in a projection of the diagonal lineshape onto ω3, shown in FIG. 11A. Two distinct peaks are observed for the sheet and coil conformations, and the helix resonance is peaked between them. The multimode structure present in the random coil spectrum is an indication that the amide II' lineshape is reporting on local backbone configurational variation rather than the longer range structure of the entire chain.

Cross peaks between amide I' and amide II' allow the new spectral features of amide II' to be assigned by correlation to understood amide I' signatures. Both upward ($\omega_1 < \omega_3$) and downward ($\omega_1 > \omega_3$) cross peaks appear. The β-sheet ZZYY spectrum shows cross peaks between both pairs of the amide I' and II' modes. The most intense cross-peak to amide I' $v_\perp$ varies with polarization; inspection of the upward cross peaks along the slice $\omega_3 = 1611$ cm$^{-1}$ shows that in ZZYY polarization the more intense cross peak is to the 1447 cm$^{-1}$ amide II' band, while in the ZZZZ polarization the cross peak to the 1470 cm$^{-1}$ amide II' band is more intense. This intensity flipping is visible, albeit more subtle, in the cross-peaks of the amide I' $v_v$ band to amide II' (along $\omega_3 = 1690$ cm$^{-1}$). The alternating intensity of the cross peaks between amide I' and II' indicates that the low frequency $v_\perp$ amide I' (1611 cm$^{-1}$) and the high frequency amide II' (1470 cm$^{-1}$) modes have aligned transition dipoles which are nearly orthogonal to those of the high frequency $v_\parallel$ amide I' (1690 cm$^{-1}$) and low frequency amide II' (1447 cm$^{-1}$) modes. In the reference frame of the protein, if the transition dipole of the more intense amide I' mode $v_\perp$ is aligned perpendicular to the β strands, then the transition dipole of the more intense amide II' mode (1447 cm$^{-1}$) is close to parallel with them.

Amide II' adds to amide I' 2D IR spectroscopy the ability to separate α-helix and random coil signatures. In addition to differences in the amide II' 2D lineshape, the random coil amide I'/II' upward and downward cross peaks are both more anti-diagonally elongated. Altogether, amide 2D IR spectroscopy allows clear separation of β sheet, α helix, and random coil structural motifs.

Figure 11B:
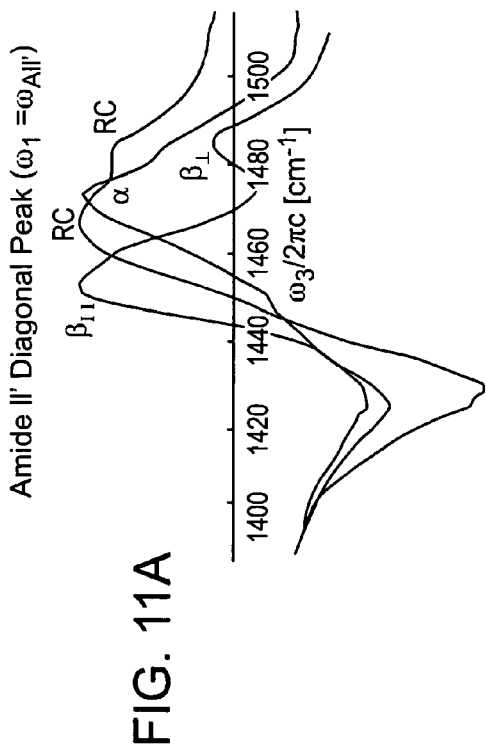
Figure 11C:
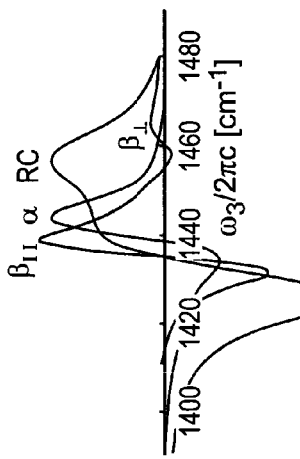
Figure 11D:
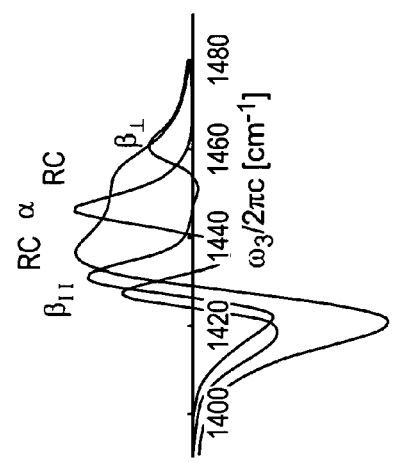
Figure 14C:
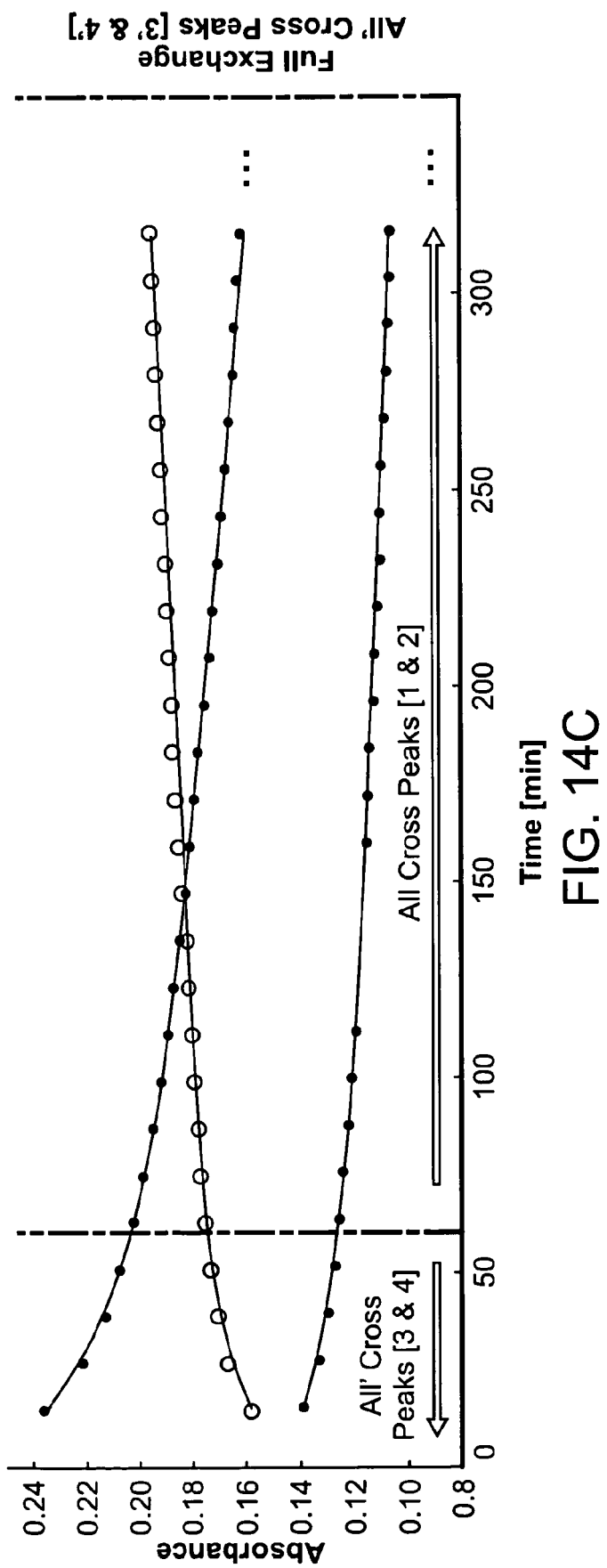
Figures 14D, 14E:
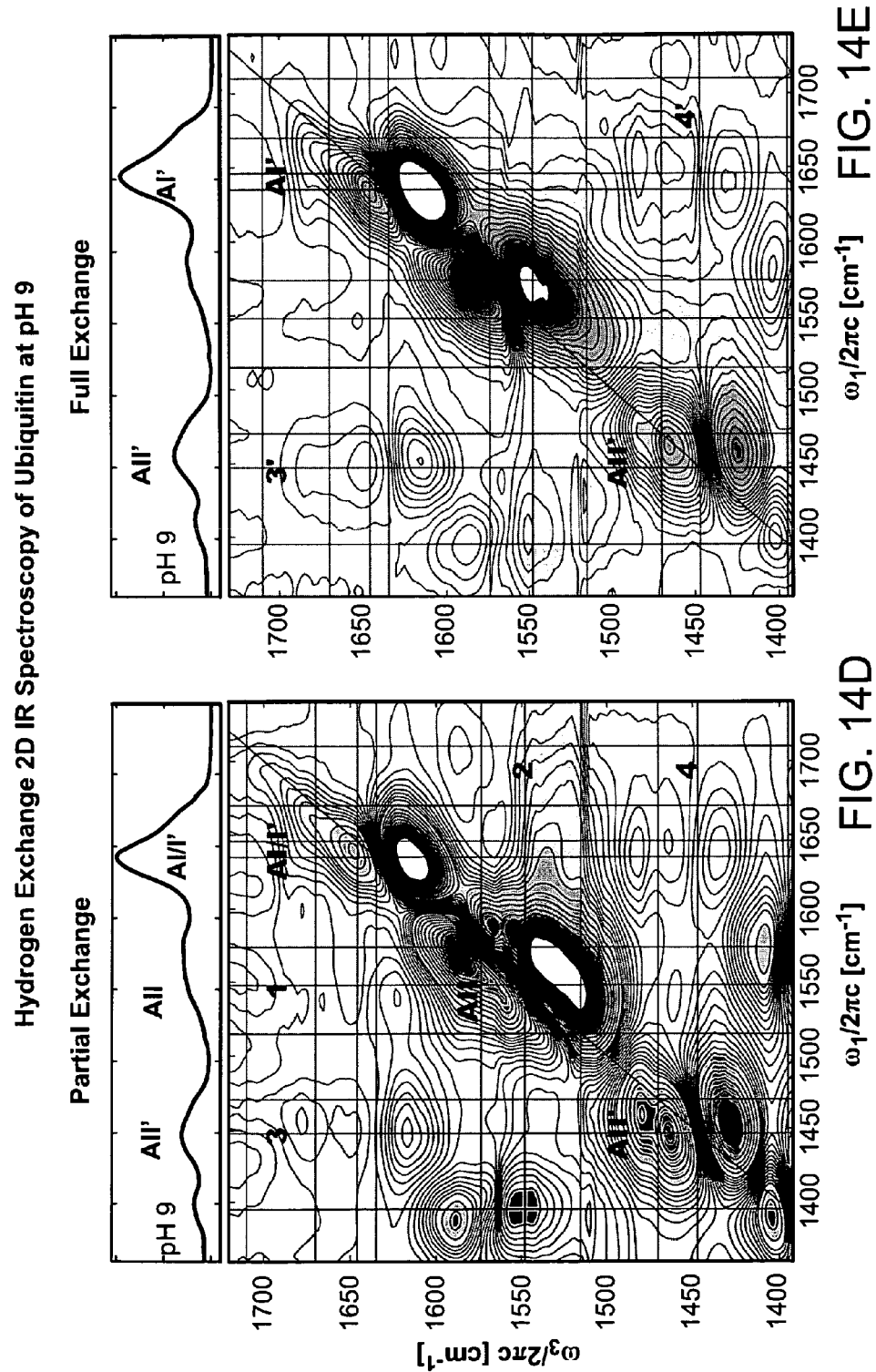
Figure 14F:
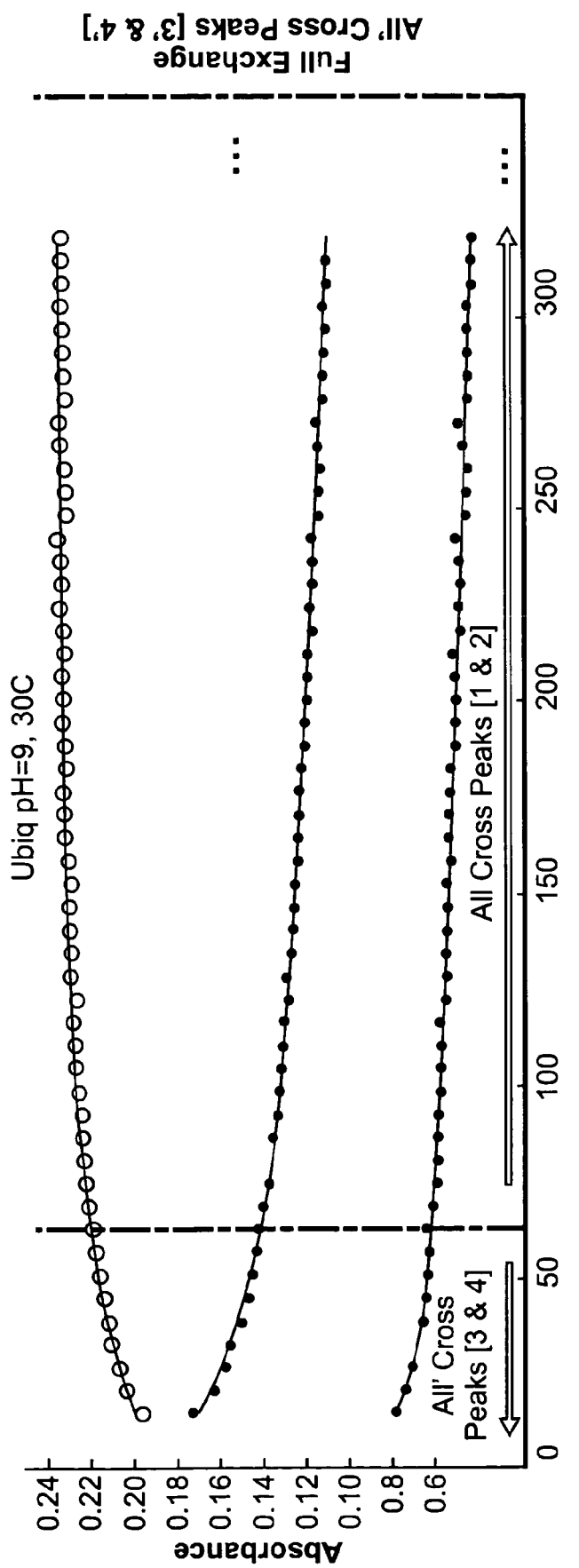

The enhanced secondary structure sensitivity of the amide I'-II' cross peak is more clearly seen as projections of the downward cross-peak lineshape onto the axis in FIG. 11B. These projections provide distinct spectral signatures for the three secondary structures. The sheet and coil both show a two peak structure, but the more intense band is red shifted for the sheet and blue shifted for the coil. The helix is dominated by one resonance that lies between the others.

Another aspect of the invention is method for determining amide I'-II' spectra of polypeptides and proteins using a structure-based representation. This representation expands the local amide Hamiltonian (LAH) approach that previously has been used to predict amide I' 2D IR spectra and to provide frequency-structure correlations. The amide I'-II' manifold of vibrations can be described as a linear combination of unit amide I' and II' oscillators on each peptide group. The LAH can be constructed on this basis, and the elements are assigned using a structure. The diagonal elements (site energy) correspond to the instrinsic vibrational frequency of that isolated oscillator, and off-diagonal terms (coupling between oscillators) depend on their separation and orientation. Diagonalizing the LAH permits calculation of FTIR and 2D IR spectra for a given structure.

The amide I' block of the local amide Hamiltonian (LAH) can be constructed, for example, as described by Torii and Tasumi (J. Chem. Phys. 1992, 96, 3379-3387). Amide II' is then added with the minimum number of extra variables. This reflects two assumptions: (1) For simplicity the amide II oscillators are assumed to couple with each other only as a result of through-bond interactions with their neighbors in the chain. This is expected given the small transition dipole moment and unfavorable position for through space amide II' couplings. (2) Similarly, amide I' and II' vibrations are assumed to only couple within the same peptide unit. This assumption is reasonable since the strength of the on-site coupling in NMA is far greater than all other interactions involving amide I and II.

Parameters for the LAH can be obtained from prior amide I'-II' 2D IR experiments on NMA-d7 in D$_2$O. See, e.g., DeFlores, L. P. et al., A. J. Phys. Chem. B 2006, 110, 18973-18980, incorporated herein by reference. The amide II' site energy can be set to $\omega_{II'} 32\ 1450$ cm$^{-1}$, the amide II' vibrational anharmonicity to $\Delta_{II'} = 10$ cm$^{-1}$, and the amide I'-II' on-site coupling to $V_{I'-II'} = 39$ cm$^{-1}$. The local amide II' transition dipole moment can also be set to a selected value. This value can be determined, for example, from the square root of the amide I'/II' extinction coefficient ratio in FTIR. To better match the random coil lineshape, the amide I' and amide II' site energies are sampled from a normal distribution with standard deviation of 10 cm$^{-1}$ about the assigned $\omega_{I'}$ and $\omega_{II'}$ values. Amide II'-II' coupling between nearest neighbor sites were set with empirically determined values to $V_{II'-II'} = -8.5$ cm$^{-1}$ for the β sheet, $-8.7$ cm$^{-1}$ for the α helix, and sampled from a normal distribution ($\langle V_{II'-II'} \rangle = -5$ cm$^{-1}$ and $\sigma = 3$ cm$^{-1}$ and a $\sigma = 3$ cm$^{-1}$) for the random coil, for example. The sign and magnitude of $V_{II'-II'}$ were constrained by the splitting and intensity of the measured cross peaks; positive coupling can be ruled out as it leads to the wrong intensity ratio between the high and low frequency features in each structural motif.

Linear and 2D IR spectra for the AP β sheet, α helix, and random coil were calculated for ZZZZ and ZZYY polarizations, and appear in FIG. 12. FTIR spectra capture the two mode structure of amide II' with different intensity variations for sheets and helices. General trends in the position and amplitude of diagonal and cross peaks, and the interference patterns they participate in were largely reproduced. Measured and calculated 2D IR spectra were also compared using projections along $\omega_1$ as shown in FIG. 11. For the random coil spectra, lineshapes and intensities of positive and negative contributions were well-reproduced by the calculation, indicating that the two peak structure is not an indicator of a random contour to the chain, but of the relatively constant through-bond coupling. The intensity of the low frequency amide II'αa helical peak is exaggerated in the calculation and appears as only a shoulder in the experiment. The splitting and intensities of the β sheet projections match the measurement reasonably well. All together these results explain the intensity variation between positive and negative lobes of the peaks without invoking electrical anharmonicity, but rather the result of interference. Agreement between the measurement and calculations demonstrates two points. First, only nearest neighbor coupling is required to reproduce the splitting between amide II' vibrations. Second, the sign and magnitude of this nearest neighbor coupling can be unambiguously obtained from the intensity ratio and splitting observed in the amide I'-II' 2D IR spectra.

Control calculations of FTIR and 2D IR spectra with and without coupling were used to examine the origin of spectral features. Amide I'-II' coupling is required for amide I'-II' cross peaks, but not to yield the observed structure in the amide II' lineshape for any of the three structural motifs. Conversely, introducing amide I'-II' coupling without amide II'-II' coupling never causes appreciable splitting in amide II'. Therefore, it was found that amide II' oscillators couple directly to neighboring amide II' oscillators; a coupling mechanism where amide II' oscillators are indirectly coupled through mutual coupling to the amide I' manifold is insufficient to reproduce any peak structure.

Using the amide II' eigenstates of the LAH, the symmetry of the vibrations contributing to the spectral features can be visualized using doorway mode analysis. This method identifies bright states that carry a majority of the oscillator strength within a restricted frequency region, and color-codes the amplitude and phase of the oscillators involved. See Chung, et al., Journal of Physical Chemistry B 2006, 110, 2888-2898; and Torii, H.; Tasumi, M. J. Chem. Phys. 1992, 97, 92-98. These doorway modes have the symmetries expected for the secondary structure. For amide II', two bright states were found that best describe the low and high frequency β-sheet modes: the amide II' sites oscillate in-phase along the β strands ($v_\parallel$) or across the β strands ($v_\perp$), respectively. For the α helix, the bright states also mirror those found for amide I' with A and E1 symmetry modes with phases aligned parallel and perpendicular to the helix axis, respectively.

The relative angles between transition dipole moments of the doorway modes were calculated for the amide I' and II' modes of the β sheet and α helix and appear in Table 1. In regions where the density of states is too low, a single intense eigenstate was selected. These results correlate very well to the observed cross peak ratios of ZZZZ and ZZYY 2D IR spectra shown in FIG. 9. As expected the strongest transitions of the amide I' and II' transitions were nearly orthogonal, with a calculated angle of 87° between the transition dipoles. Similarly, the dominant α-helix mode of amide I' runs along the axis while the dominant amide II' is orthogonal. This is observed in both the calculated angles of the amide I A mode relative to the E1 modes of amide II' of 72° and 92° and in the measured polarization spectra.

TABLE 1

Calculated angles between the amide I' and II' doorways modes and eigenstates.

| | | Amide II' | | | | |
|---|---|---|---|---|---|---|
| | θ | $v_p$ 1425 cm$^{-1}$ | $v_{perp}$ 1460 cm$^{-1}$ | A 1426 cm$^{-1}$ | E$_1$ 1444 cm$^{-1}$ | E$_1$ 1446 cm$^{-1}$ |
| Amide I' | θ | 91 | 2 | 159 | 92 | 112 |
| | $v_{11}$ 1680 cm$^{-1}$ | 61 | 30 | −59 | | |
| | $v_{perp}$ 1640 cm$^{-1}$ | 177 | −87 | −175 | | |

TABLE 1-continued

Calculated angles between the amide I' and II' doorways modes and eigenstates.

| | | Amide II' | | | | |
|---|---|---|---|---|---|---|
| | θ | $v_p$ 1425 cm$^{-1}$ | $v_{perp}$ 1460 cm$^{-1}$ | A 1426 cm$^{-1}$ | E$_1$ 1444 cm$^{-1}$ | E$_1$ 1446 cm$^{-1}$ |
| A 1645 cm$^{-1}$ | 20 | | | 139 | 72 | 92 |
| E$_1$ 1650 cm$^{-1}$ | 60 | | | 99 | 32 | 52 |
| E$_1$ 1657 cm$^{-1}$ | 69 | | | 89 | 23 | 43 |

For each mode, the central frequency of the doorway mode is given (for single frequencies the angle of the eigenstates is used), the dipole moment intensity and the angle relative to the +Y (for β-sheet) and +Z (for α-helix). θ defines the angles of the transition dipole relative to the dominant axis of the secondary structure. Bolded angles represent modes with the strongest cross peaks observed in the ZZYY 2D IR spectra.

The full 2D IR spectrum of the amide I/I'/II/II' finger print region provides a wealth of information about protein solvation and structure. By using 2D IR, one has the ability to correlate different sensitivities of vibrationally coupled modes through the presence of cross peaks. Each cross peak provides a different vantage point and allows for simultaneous acquisition of information. The intensity of the cross peak depends on the strength of coupling and the relative angle of the transition dipole moment. The frequency reports on the modes that are coupled.

Hydrogen-deuterium exchange (HX) spectroscopy is a further example of the use of amide I/I'/II/II' spectroscopy for characterizing protein secondary structure, structural stability, solvation and water exposure, and unfolding kinetics. HX is influenced by the site specific $pK_A$, solvent accessibility to protonated sites and strength of hydrogen bonding interactions. In the hydrophobic core or strongly hydrogen bound secondary structures, HX rates are dramatically reduced due to shielding of exchangeable sites. NMR methods infer the degree of protection and structural stability from site-specific HX measurements, which can be incorporated into fast-mixing experiments to provide the information about reaction intermediates. IR spectroscopy in conjunction with HX also provides information on solvent exposure of the protein backbone, relying on the strong red shift of the amide II vibration upon deuteration of the peptide group NH. IR is an appealing technique for kinetic studies, since it can be used in combination with fast unfolding measurements. However, amide II is not otherwise structurally sensitive and is typically overlapped with side-chain absorptions. Using two-dimensional infrared (2DIR) spectroscopy, HX experiments that combine the solvent-exposure sensitivity of amide II and II' with the secondary-structure sensitivity of amide I and I'. The correlation of transition frequencies in the amide I-II region provides a secondary structure sensitive probe of protein solvent accessibility ideal for studies of protein folding and stability.

For the HX measurements, under partial exchange each 2D IR spectra has the dominate diagonal resonances, the amide I/I', II and II' modes. The amide I/I'-II cross peak will be sensitive to secondary structure that is solvent inaccessible, while the amide I/I'-II' cross peak will isolate residues that have undergone hydrogen-deuterium exchange. Amide I'-II' coupling will be stronger than amide I-II due to the local mode composition of the vibrational bands.

The relative angle of the amide II band (assumed to be a localized to the amide group and 65° from the CO bond) will lie 60° and 55° with respect to the amide I/I' $v_\perp$ and $v_{II}$ modes and 95° relative to the amide I A mode of the α-helix. The amide II' band is shown to exhibit secondary structure sensitivity. The two β-sheet amide II' signatures have an inclusive angle of 88°. The dominant amide II' mode along the β strands is calculated to be 86° relative to $\gamma_\perp$ and 30° relative to $v_{II}$ of amide I/I'. The degenerate α-helix $E_1$ modes of amide II' lie 92° and 112° off the central axis of the helix. This gives a relative angle of 72° and 92° to the A mode of the amide I helix. In the ZZYY spectra, purely based on the angular dependence, the amide I/I'-II' cross peak will show strong transition indicative of coupling between the along the strand mode of amide II' and $\sigma_\perp$ mode of amide I, as well as a strong helical cross peak. The amide I/I'-II cross peak will show strong helical coupling and relatively weaker β-sheet peaks.

To demonstrate the stability of secondary structure elements of ubiquitin, pH dependent 2D IR spectra were taken under partial and full exchange. At pH 6.7, ubiquitin's isoelectric point, the protein is the most stable and has been shown to have melting points exceeding 100° C. at higher pH. FIGS. 14A-14F show the full 2D IR amide I/I'/II/II' spectrum of ubiquitin under partial exchange at 5° C. and the fully exchange spectra at both pH 1 and 9. Glutamic acid has a symmetric and asymmetric mode at 1400 cm$^{-1}$ and 1586 cm$^{-1}$ at pH 9. For the partially exchanged spectra, peaks 1 and 2 are the amide I/I'-II upward and downward cross peaks. These peaks report on solvent inaccessible protons and, therefore, label amide protons that have not exchange prior to experimental acquisition (approximately 60 minutes). Peaks 3 and 4 report on the amide protons that have exchanged and therefore solvent accessible regions. Peaks 3' and 4' of the fully exchange spectra (FIGS. 14B and 14E) report on the coupling of amide I'-II' of the full protein. In these spectra, the amide II diagonal and off-diagonal peaks no longer exist.

Visual inspection of the partially exchanged 2D spectra (FIGS. 14A-14D), directly indicate that pH 9 has exchanged more readily than pH 1 in one hour. This can be seen by directly comparing the relative cross peak intensities of the upward amid II and II' bands (peaks 1 and 3).

To gain further insight into the regions of the protein that have exchanged, the structure of the cross peaks is analyzed. Projections of the amide II' diagonal and the amide I/I'-II and -II' cross peaks (1, 3, 4 and 4'). Inspection of the amide II' diagonal for both pH 1 and 9 (FIGS. 15A and 15B) show a random coil line shape. Therefore, there is no global exchange of secondary structure. This implies that only random coil regions of the protein, isolated amide units of protein secondary structure or both have exchanged. Upon fill exchange three additional peaks appear that correspond to the exchange of the β sheet (1440 cm$^{-1}$ and 1484 cm$^{-1}$ shoulders) and the α helix at 1470 cm$^{-1}$. The increased secondary structure content of the amide II' diagonal upon full exchange is also reflected in the upward cross peak seen as a shift of the combination band (negative peak) from 1450 cm$^{-1}$ to 1458 cm$^{-1}$. This shift reflects the coupling of the deuterated α-helix.

The amide I/I'-II cross peaks (4 and 4') show similar features to the amide II' diagonal. Displacements of peaks along $\Omega_{d1}$ projection onto the amide I band provide more insight into exchanged secondary structure. However, the signal to noise is insufficient in this data set. Alternatively, the upward cross peak provides identical information.

Figures 15E, 15F:
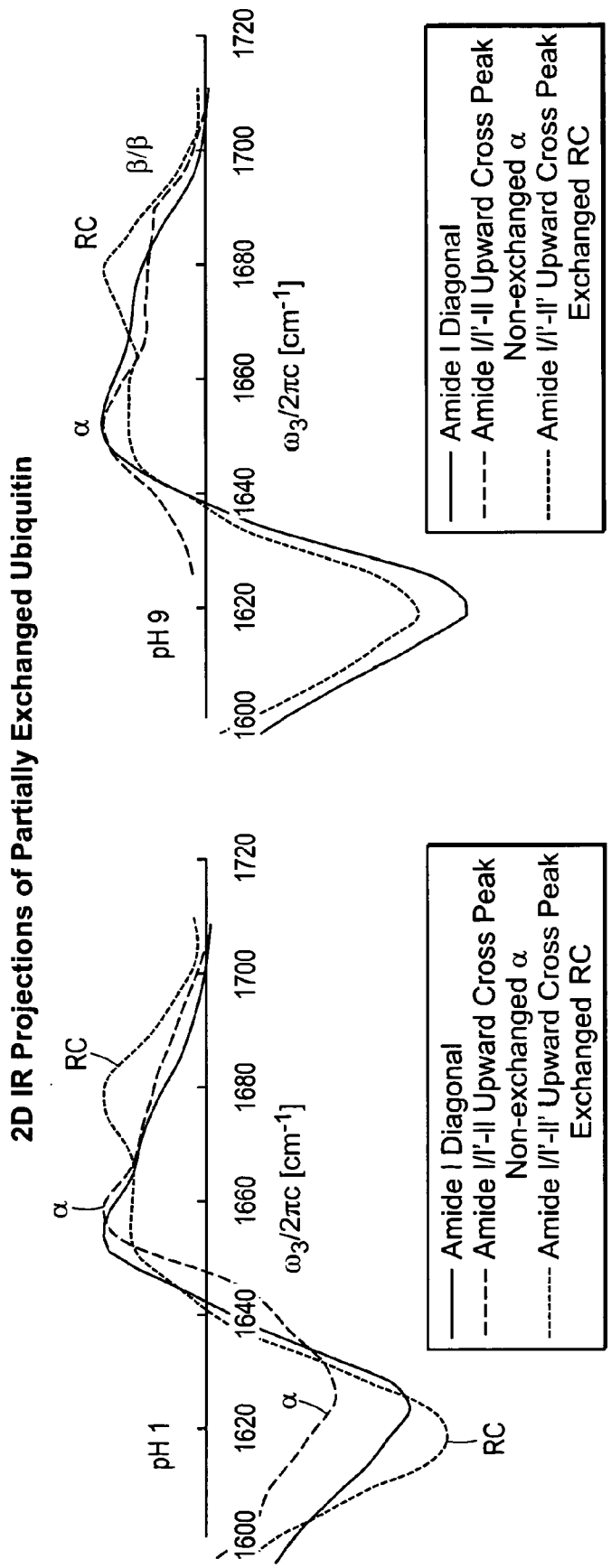
Figures 16A, 16B:
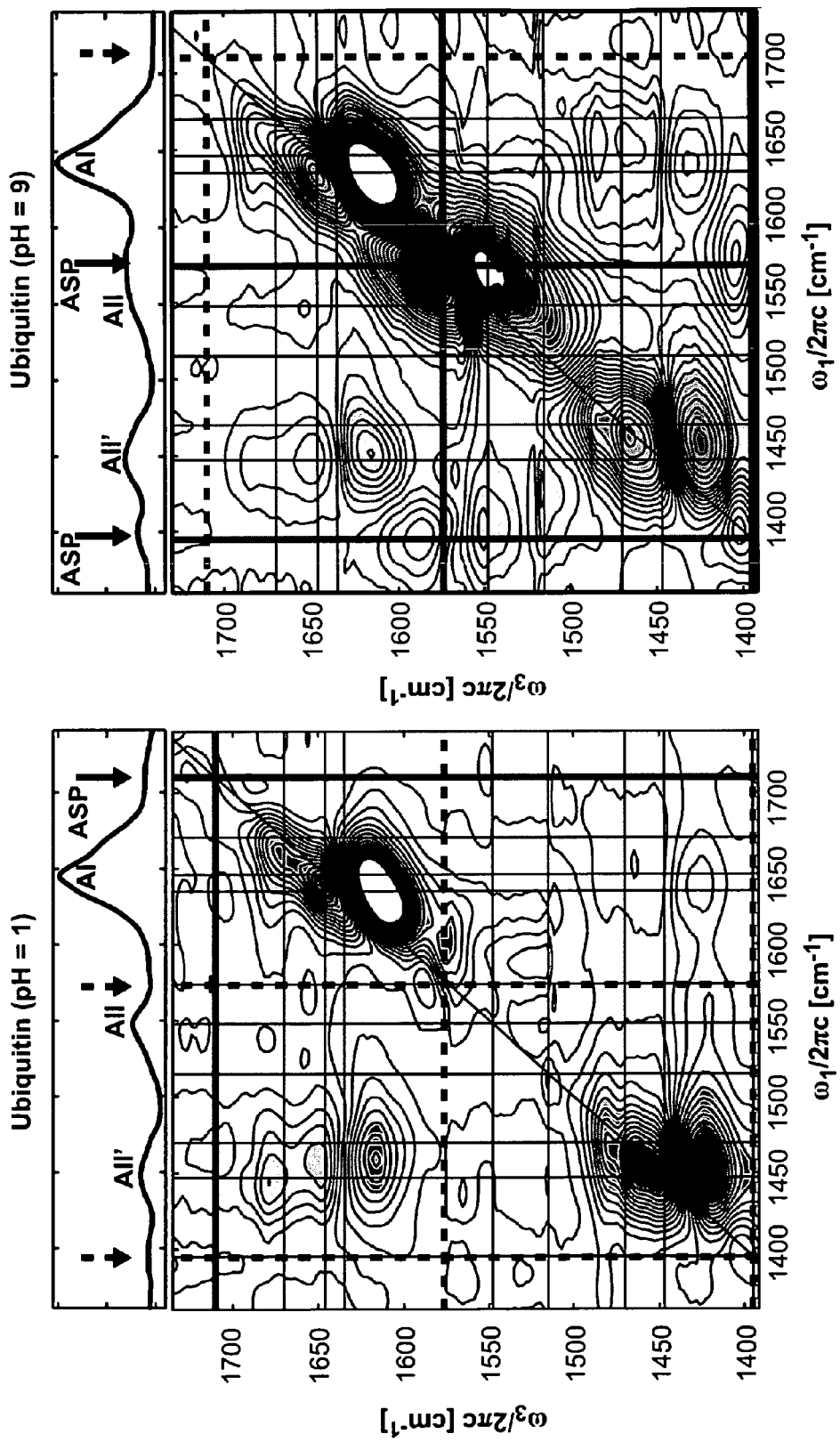
FIGS. 16A-16G include FTIR and 2DIR spectra showing the aspartic acid side chain absorption in ubiquitin at pH=1 (FIG. 16A) and pH=9 (FIG. 16B), Concanavalin A (FIG. 16C), and Myoglobin (FIG. 16D).
Figure 16C:
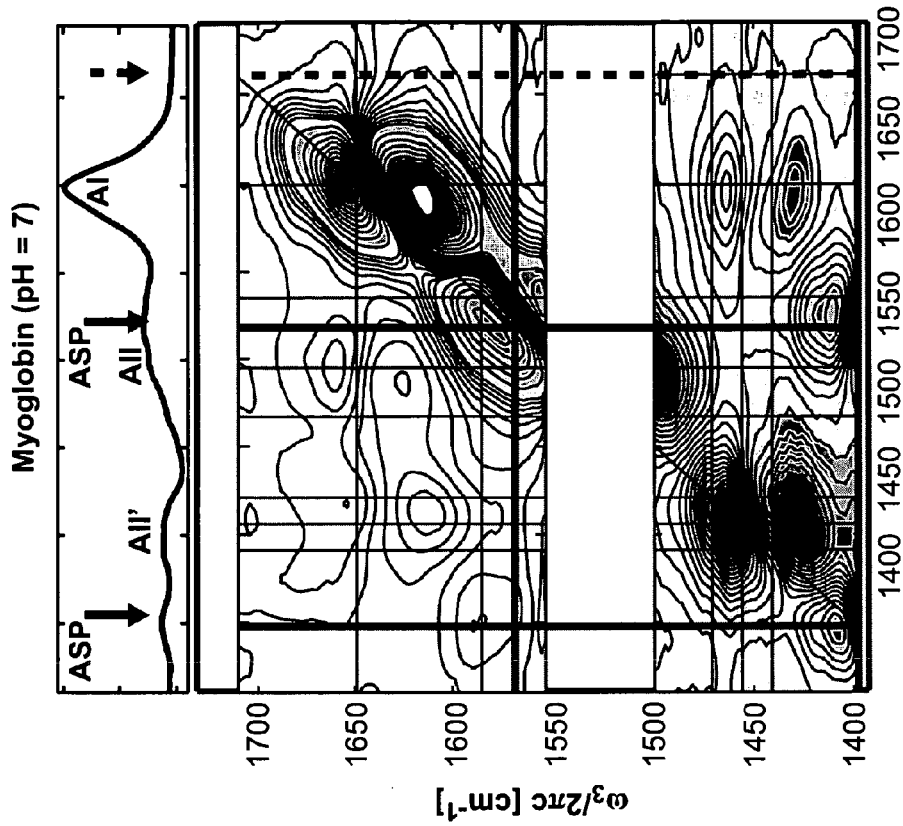
Figure 16D:
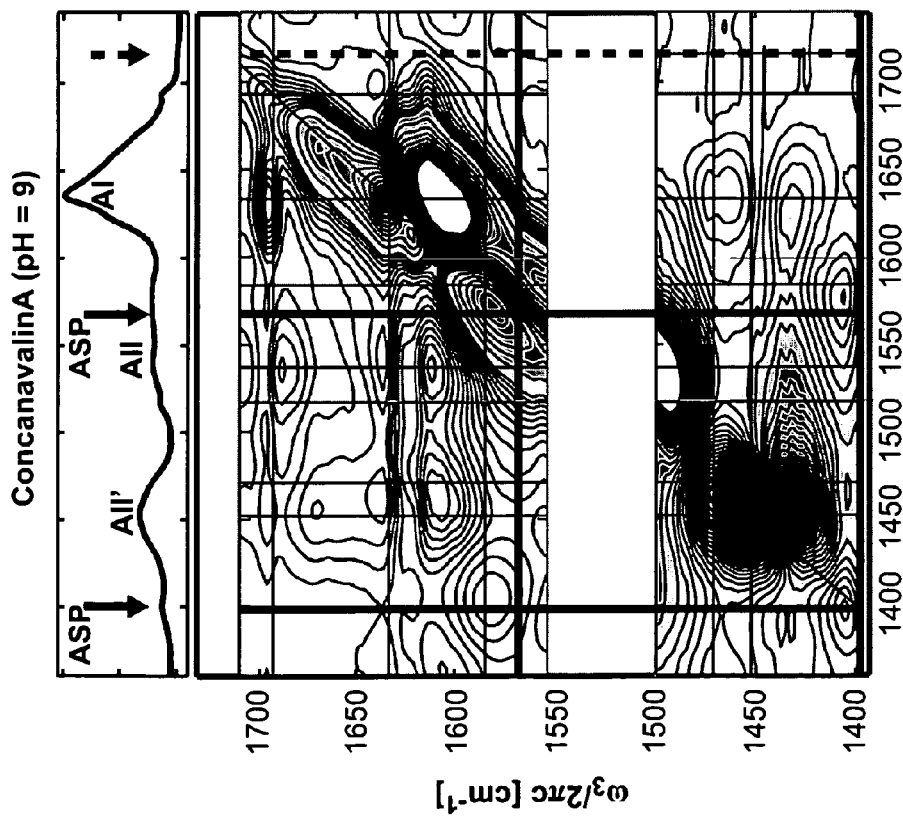
Figures 16E, 16F, 16G:
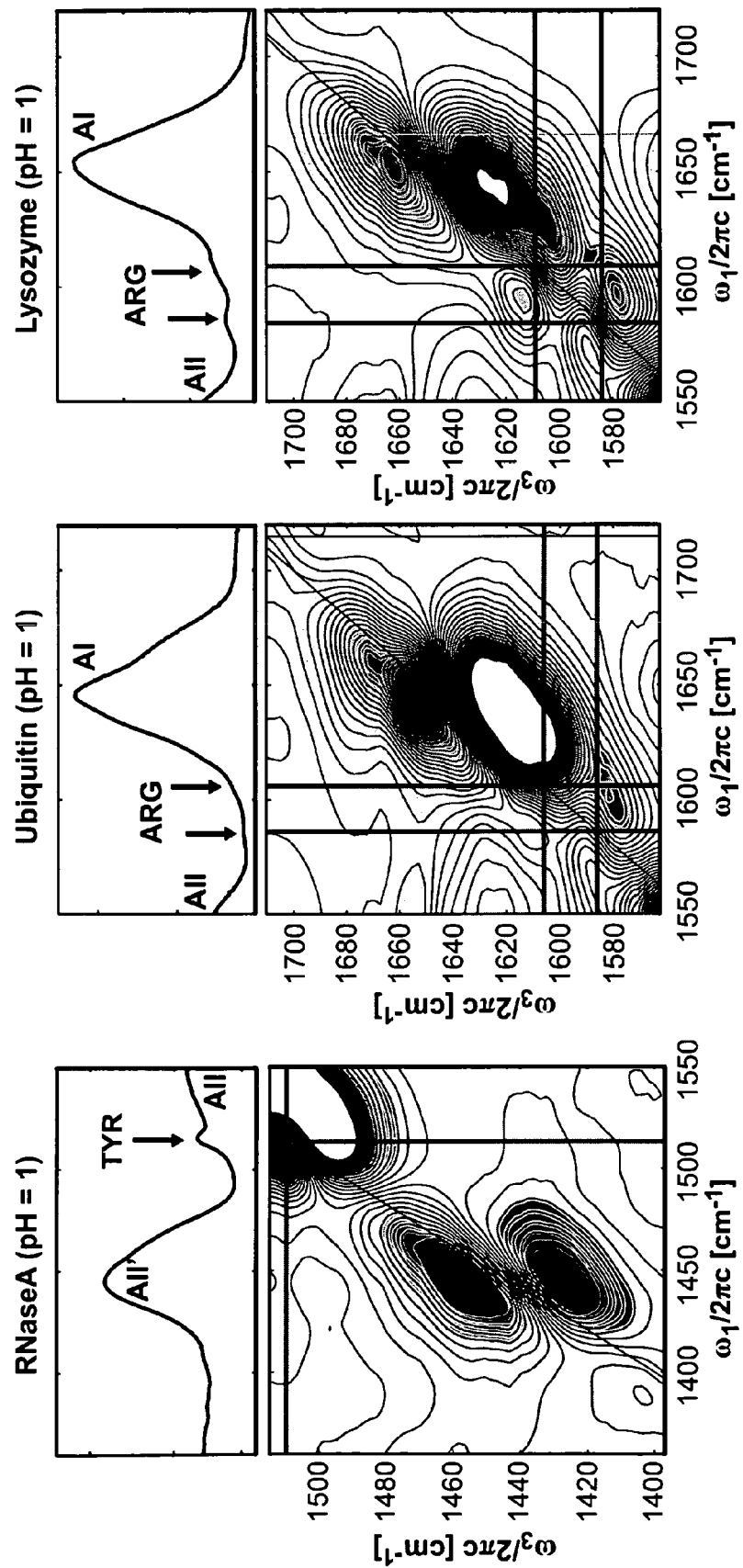

To determine if isolated residues in secondary structure have exchanged in these systems, the amide I/I' diagonal is compared to the amide I/I'-II and -II' cross peaks in FIGS. 15E and 15F. The blue traces, or the amide I/I'-II' cross peak, reports on solvent exposed residues and show clear random coil signatures. As expected, the random coil regions are highly solvated and are expected to rapidly exchange. Additionally, the red traces, or the amide I/I'-II cross peak that report on solvent inaccessible residues, show clear helical features at 1655 cm$^{-1}$. Helices contain particularly strong hydrogen bonds, and for ubiquitin, the helix is an integral part of the hydrophobic core and is expected to exchange less rapidly due to structural stability. In the pH 9 projections, signatures of partial β-sheet exchange are seen as a small peak near 1690 cm$^{-1}$. Joining the signature of the amide II' diagonal and the appearance of β-sheet signature in both cross peaks reveals that isolated residues of the β-sheet are exchanging. For the low pH system, the broadening seen between the red and blue trace at 1645 cm$^{-1}$ suggests that a significant portion of the β-sheet has exchanged. However, due to the structure of the amide II' diagonal, the number of sites exchange still does not provide the proper nearest neighbor structure of amide II' oscillators to generate substantial structural sensitivity.

In addition to the amide vibrations, sides chains with carboxyl, aliphatic, and aromatic groups absorb in the infrared spectrum. Side chains play a vital role in protein stability through structural contacts and in function for the catalysis of enzymatic reactions. The vibrational signatures of side chains are strongly influenced by the local protein and solvent environment. Hydrogen bonding will induce spectra shifts, as will protonation state and coordination of cations. These factors will also influence absorption coefficients and spectral line widths. Through the use of 2D IR coupling of side chains and the amide backbone vibrations can be exploited to reveal more information about protein structure and enzymatic function. First, however, the side chain vibrational signatures must be identified and characterized. Table 2 details the extinction coefficients and peak frequencies of the amino acid side chains that absorb in the amide fingerprint region as detailed by Barth and co-workers. 2D IR spectra can be used to assist in the assignment within congested IR spectra and reveal couplings of protein side chains with side chains and/or the main chain. In FIGS. 16A-16G, the 2D IR spectra are presented of aspartic acid, tyrosine and arginine in a number of proteins.

TABLE 2A

Side Chain Absorptions in H$_2$O

| Amino Acid | | | cm$^{-1}$ (H$_2$O) < pK$_s$ low pH | | cm$^{-1}$ (H$_2$O) | cm$^{-1}$ (H$_2$O) > pK$_s$ high pH | | Mode | pK$_s$ |
|---|---|---|---|---|---|---|---|---|---|
| Arginine | ARG | R | 460 | 1652 | — | — | — | $v_{as}CN_3H_5^+$ | 11.6-12.6 |
| | | | 320 | 1630 | — | — | — | $v_sCN_3H_5^+$ | |
| Aspartic Acid | ASP | D | — | — | 280 | 1716 | | $vC=O$ | 4.0-4.8 |
| | | | — | — | — | — | 235 | 1577 | $v_{as}COO^-$ | |
| | | | — | — | — | — | 256 | 1402 | $v_sCOO^-$ | |

TABLE 2A-continued

Side Chain Absorptions in H₂O

| Amino Acid | | | cm⁻¹ (H₂O) < pK$_s$ low pH | | cm⁻¹ (H₂O) | | cm⁻¹ (H₂O) > pK$_s$ high pH | | Mode | pK$_s$ |
|---|---|---|---|---|---|---|---|---|---|---|
| | | | — | — | — | 1375 | — | — | $\delta_s$CH$_3$ | |
| Asparagine | ASN | N | — | — | 320 | 1677 | — | — | $\nu$C=O | |
| | | | — | — | 150 | 1617 | — | — | $\delta$NH$_2$ | |
| Cysteine | CYS | C | — | — | — | 2551 | — | — | $\nu$SH | 9.0-9.5 |
| Glutamic Acid | GLU | E | — | — | 220 | 1712 | — | — | $\nu$C=O | 4.4-4.6 |
| | | | — | — | — | — | 460 | 1558 | $\nu_{as}$COO⁻ | |
| | | | — | — | — | — | 316 | 1404 | $\nu_s$COO⁻ | |
| Glutamine | GLN | Q | — | — | 370 | 1680 | — | — | $\nu$C=O | |
| | | | — | — | 230 | 1595 | — | — | $\delta$NH$_2$ | |
| | | | — | — | — | 1410 | — | — | $\nu$CN | |
| Histindine | HIS | H | 250 | 1631 | — | — | — | — | $\nu$C=C (H$_2^+$) | 6.0-7.0 |
| | | | 70 | 1575, 1594 | — | — | — | — | $\nu$C=C (H) | |
| | | | — | — | — | — | — | 1439 | $\delta$CH$_3$, $\nu$CN (⁻) | |
| Lysine | LYS | K | 80 | 1626 | — | — | — | — | $\delta_{as}$NH$_3^+$ | 10.4-11.1 |
| | | | 85 | 1526 | — | — | — | — | $\delta_s$NH$_3^+$ | |
| Phenylalanine | PHE | F | — | — | 80 | 1494 | — | — | $\nu$CC ring | |
| | | | — | — | — | 1460 | — | — | $\delta_{as}$CH$_3$ | |
| Proline | PRO | P | — | — | — | 1432 | — | — | $\nu$CN | |
| | | | — | — | — | 1450 | — | — | $\delta$CH$_2$ | |
| Tryptophan | TRP | W | — | — | — | 1622 | — | — | $\nu$CC, $\nu$C=C | |
| | | | — | — | — | 1509 | — | — | $\nu$CN, $\delta$CH, $\delta$NH | |
| | | | — | — | — | 1496 | — | — | $\nu$CC, $\delta$CH | |
| | | | — | — | — | 1462 | — | — | $\delta$CH, $\nu$CC, $\nu$CN | |
| | | | — | — | — | 1427 | — | — | dNH, $\nu$CC, $\delta$CH | |
| Tyrosine | TYR | Y | 120 | 1617 | — | — | — | — | $\nu$CC, $\nu$CH | 9.8-10.4 |
| | | | 85 | 1598 | — | — | 160 | 1601 | $\nu$CC | |
| | | | 385 | 1515 | — | — | — | — | $\nu$CC, $\delta$CH | |
| | | | — | — | — | — | 700 | 1499 | $\nu$CC, $\delta$CH | |
| | | | — | — | — | — | 580 | 1270 | $\nu$CO, $\delta$CC | |
| | | | 200 | 1250 | — | — | — | — | $\nu$CO, $\delta$CC | |

TABLE 2B

Side Chain Absorptions in D₂O

| Amino Acid | | | cm⁻¹ (D$_2$O) < pK$_s$ low pH | | cm⁻¹ (D$_2$O) | | cm⁻¹ (D$_2$O) > pK$_s$ high pH | | Mode | pK$_s$ (pH) |
|---|---|---|---|---|---|---|---|---|---|---|
| Arginine | ARG | R | 460 | 1605 | — | — | — | — | $\nu_{as}$CN$_3$D$_5^+$ | 11.6-12.6 |
| | | | 500 | 1586 | — | — | — | — | $\nu_s$CN$_3$D$_5^+$ | |
| Aspartic Acid | ASP | D | — | — | 290 | 1713 | — | — | $\nu$C=O | 4.0-4.8 |
| | | | — | — | — | — | 820 | 1584 | $\nu_{as}$COO⁻ | |
| | | | — | — | — | — | — | 1404 | $\nu_s$COO⁻ | |
| Asparagine | ASN | N | — | — | 570 | 1648 | — | — | $\nu$C=O | |
| Cysteine | CYS | C | — | — | — | 1849 | — | — | $\nu$SD | 9.0-9.5 |
| Glutamic Acid | GLU | E | — | — | 280 | 1706 | — | — | $\nu$C=O | 4.4-4.6 |
| | | | — | — | — | — | 830 | 1567 | $\nu_{as}$COO⁻ | |
| | | | — | — | — | — | — | 1407 | $\nu_s$COO⁻ | |
| Glutamine | GLN | Q | — | — | 550 | 1640 | — | — | $\nu$C=O | |
| | | | — | — | — | 1163 | — | — | $\delta$ND$_2$ | |
| | | | — | — | — | 1409 | — | — | $\nu$CN | |
| Histindine | HIS | H | 35 | 1600 | — | — | — | — | $\nu$C=C (D$_2^+$) | 6.0-7.0 |
| | | | 70 | 1569, 1575 | — | — | — | — | $\nu$C=C (D) | |
| | | | — | — | — | — | — | 1439 | $\delta$CD$_3$, $\nu$CN (⁻) | |
| Lysine | LYS | K | — | 1200 | — | — | — | — | $\delta_{as}$ND$_3^+$ | 10.4-11.1 |
| | | | — | 1170 | — | — | — | — | $\delta_s$ND$_3^+$ | |
| Tryptophan | TRP | W | — | — | — | 1618 | — | — | $\nu$CC, $\nu$C=C | |
| | | | — | — | 200 | 1455 | — | — | $\delta$CD, $\nu$CC, $\nu$CN | |
| | | | — | — | — | 1382 | — | — | $\delta$ND, $\nu$CC, $\delta$CD | |
| Tyrosine | TYR | Y | 160 | 1615 | — | — | — | — | $\nu$CC, $\nu$CD | 9.8-10.4 |
| | | | 50 | 1590 | — | — | 350 | 1630 | $\nu$CC | |
| | | | 500 | 1515 | — | — | — | — | $\nu$CC, $\delta$CD | |
| | | | — | — | — | — | 650 | 1499 | $\nu$CC, $\delta$CD | |
| | | | 150 | 1255 | — | — | — | — | $\nu$CO, $\delta$CC | |

Extinction coefficients and peak frequencies of amino acids that absorb between 1200 cm⁻¹ and 1800 cm⁻¹ in H$_2$O and D$_2$O. Frequencies are tabulated as a function of pH relative to the pK$_a$ value determined from the isolated amino acid. For vibrations with no pH dependence appear in the central column.

While the present invention has been described herein in conjunction with a preferred embodiment, a person with ordinary skill in the art, after reading the foregoing specification, can effect changes, substitutions of equivalents and other types of alterations to the system and method that are set forth herein. Each embodiment described above can also have included or incorporated therewith such variations as disclosed in regard to any or all of the other embodiments. Thus, it is intended that protection granted by Letters Patent hereon be limited in breadth only by definitions contained in the appended claims and any equivalents thereof.

What is claimed is:

1. A two dimensional spectroscopic system comprising:
a light source that emits light;
an optical system coupled to the light source that directs a collinear pulse sequence onto a medium;
an optical signal that is optically coupled to the medium to modulate light directed onto the medium;
a dispersion element that disperses a modulated optical signal from the medium; and
a detector that detects the dispersed modulated optical signal to provide a spectral representation having a plurality of dimensions.

2. The system of claim 1 further comprising a processor that processes spectral data to provide the spectral representation.

3. The system of claim 2 wherein the processor executes a program that performs a transformation of the spectral data.

4. The system of claim 1 wherein the optical system includes an optical combiner that combines a plurality of light pulses from a first optical path and a second optical path to form the collinear pulse sequence along a third optical path, such that rephasing and non-rephasing spectral data are detected by the detector.

5. The system of claim 4 further comprising a second detector that detects light from the first optical path and the second optical path for interferometric autocorrelation.

6. The system of claim 1 further comprising a third detector for measuring stage calibration data.

7. The system of claim 1 wherein the optical system further comprises an optical delay element and an actuator that adjusts an optical delay along a first beam path from the light source.

8. The system of claim 7 further comprising a second optical delay element and a second actuator adjusting an optical delay along a second beam path from an optical splitter.

9. The system of claim 1 further comprising an optical signal delay element and a signal delay actuator that adjusts an optical path length of the optical signal.

10. The system of claim 1 wherein the optical system comprises:
an optical splitter that separates light from the light source along a first beam path and along a second beam path;
an actuator that adjusts relative beam delay between the first beam path and the second beam path;
an optical combiner that combines light directed along the first beam path with light directed along the second beam path to form a third beam path that is optically coupled to a medium.

11. The system of claim 10 further comprising a second beam splitter that directs light along a third optical delay path.

12. The system of claim 1 wherein the optical system comprises a first beam delay element, a second beam delay element and a third beam delay element.

13. The system of claim 1 wherein the dispersion element generates a heterodyned signal that is detected by the detector.

14. The system of claim 10 further comprising a course time delay element and a fine time delay element.

15. The system of claim 10 wherein a time delay element comprises a moveable material having variable thickness.

16. The system of claim 10 wherein a time delay element comprises a retroreflector.

17. The system of claim 1 further comprising a spectrometer.

18. A method of measuring a spectrum having a plurality of dimensions comprising:
coupling a collinear sequence of light pulses onto a medium;
coupling an optical signal onto the medium, the optical signal being modulated by the sequence of light pulses to form a modulated light signal;
dispersing the modulated light signal;
detecting the dispersed modulated light signal to provide spectral data; and
forming a spectral representation from the spectral data having a plurality of dimensions.

19. The method of claim 18 further comprising performing a Fourier transformation of the spectral data to form a spectral representation having a first frequency along a first dimension and a second frequency along a second dimension.

20. The method of claim 18 further comprising providing the sequence of light pulses at a first frequency and providing an optical signal at a second frequency.

21. The method of claim 18 further comprising polarizing the optical signal and adjusting an analyzer to detect a dispersive component of the modulated optical signal.

22. The method of claim 18 further comprising adjusting an optical delay of a pulse in the sequence of light pulses to scan the medium.

23. The method of claim 18, wherein the medium comprises a polypeptide or protein, and the method further comprises analyzing the spectral representation to characterize a secondary structure of the polypeptide or protein.

24. The method of claim 23, regarding wherein the step of analyzing provides information regarding one or the more amide vibrational states.

25. The method of claim 24, wherein the one or more amide vibrational states are selected from the group consisting of amide I, amide II, amide I', and amide II'.

26. The method of claim 25, wherein information is provided regarding both amide I' and amide II' vibrational states.

27. The method of claim 23, wherein the secondary structure comprises a-helix, sheet, or random coil structure.

28. The method of claim 18 wherein the medium comprises a polypeptide or protein and the method further comprises analyzing a sidechain.

29. The method of claim 28 further comprising analyzing a protonation state of the sidechain.

30. The method of claim 28 further comprising analyzing a deuteration state of the sidechain.

31. The method of claim 28 further comprising analyzing a sidechain absorption spectrum.

32. The method of claim 25 wherein each of the vibrational states is analyzed.

33. The method of claim 25 further comprising determining water exposure of a protein secondary structure.

34. The method of claim 18 further comprising measuring a time-resolved spectrum.

35. The method of claim 34 further comprising analyzing the time resolved spectrum to determine water exposure of a protein.

36. The system of claim 2 further comprising a computer program stored in a memory to process image data with the processor.

37. The system of claim 1 further comprising a pulse stretcher.

38. The system of claim 1 further comprising a pulse compressor.

39. The system of claim 1 further comprising a polarizer to control pulse polarization.

40. The system of claim 1 further comprising a waveplate to adjust pulse intensity.

41. A system for generating spectral data having a plurality of dimensions comprising:
- a light source that emits light;
- an optical system coupled to the light source that directs a collinear pulse sequence onto a medium;
- an optical signal that is optically coupled to the medium to modulate light directed onto the medium; and
- a detector that detects a modulated optical signal to provide spectral data having a plurality of dimensions.

42. The system of claim 41 further comprising a processor connected to the detector such that the processor processes the spectral data.

43. The system of claim 42 wherein the processor includes a program that performs a transformation of the spectral data.

44. The system of claim 41 wherein the optical system includes an optical combiner that combines a plurality of light pulses from a first optical path and a second optical path to form the collinear pulse sequence along a third optical path.

45. The system of claim 41 further comprising a second detector that detects light from the first optical path and the second optical path for interferometric autocorrelation.

46. The system of claim 41 further comprising a third detector for measuring stage calibration data.

47. The system of claim 41 wherein the optical system further comprises an optical delay element and an actuator that adjusts an optical delay along a first beam path from the light source.

48. The system of claim 47 further comprising a second optical delay element and a second actuator adjusting an optical delay along a second beam path.

49. The system of claim 41 further comprising an optical signal delay element and a signal delay actuator that adjusts an optical path length of the optical signal.

50. A pulse modulation system comprising:
- an optical system that directs a collinear pulse sequence onto a medium;
- an optical signal that is optically coupled to the medium to modulate light directed onto the medium;
- a pulse modulation system to modulate at least one light pulse incident on the medium; and
- a detector that detects the modulated optical signal to provide a spectral data having a plurality of dimensions.

51. The system of claim 50 further comprising a processor that processes the spectral data from the detector.

52. The system of claim 51 wherein the processor executes a program that performs a transformation of the spectral data.

53. The system of claim 52 wherein the optical system includes an optical combiner that combines a plurality of light pulses from a first optical path and a second optical path to form the collinear pulse sequence along a third optical path.

54. The system of claim 50 wherein the pulse modulation system further comprises an optical delay element and an actuator that adjusts an optical delay along a first beam path.

55. The system of claim 50 wherein the pulse modulation system further comprises a second optical delay element and a second actuator adjusting an optical delay along a second beam path.

56. The system of claim 50 wherein the pulse modulation system further comprises an optical signal delay element and a signal delay actuator that adjusts an optical path length of an optical signal.

57. The system of claim 50 wherein the pulse modulation system comprises a pulse stretcher.

58. A method of measuring spectral data having a plurality of dimensions comprising:
- coupling a collinear sequence of light pulses onto a medium;
- coupling an optical signal onto the medium, the optical signal being modulated by the sequence of light pulses to form a modulated light signal;
- detecting the modulated light signal to provide spectral data; and
- processing the spectral data having a plurality of dimensions.

59. The method of claim 58 further comprising detecting light received from the medium that includes a protein.

60. The method of claim 59 wherein the spectral data represents a protein secondary structure.

61. The method of claim 59 further comprising detecting infrared cross peaks.

62. The method of claim 59 further comprising detecting a peptide in the medium.

* * * * *

UNITED STATES PATENT AND TRADEMARK OFFICE
CERTIFICATE OF CORRECTION

PATENT NO. : 8,526,002 B2  
APPLICATION NO. : 12/676536  
DATED : September 3, 2013  
INVENTOR(S) : Lauren DeFlores et al.

Page 1 of 1

It is certified that error appears in the above-identified patent and that said Letters Patent is hereby corrected as shown below:

Title page Item (60) Should read:

\*\* Related U.S. Application Data

Provisional Application No. 60/967,889 filed on September 7, 2007 \*\*

Signed and Sealed this
Thirteenth Day of September, 2016

Michelle K. Lee
*Director of the United States Patent and Trademark Office*